US012073929B2

(12) United States Patent
Bhansali et al.

(10) Patent No.: US 12,073,929 B2
(45) Date of Patent: Aug. 27, 2024

(54) REAL TIME PARSER FOR USE WITH ELECTRONIC MEDICAL RECORDS

(71) Applicant: MedAmerica Data Services, LLC, Emeryville, CA (US)

(72) Inventors: Vivek Bhansali, San Jose, CA (US); David Yue, Union City, CA (US); Dipti Patel-Misra, Alamo, CA (US); Joshua Tamayo-Sarver, Los Gatos, CA (US)

(73) Assignee: MEDAMERICA DATA SERVICES, LLC, Emeryville, CA (US)

( * ) Notice: Subject to any disclaimer, the term of this patent is extended or adjusted under 35 U.S.C. 154(b) by 0 days.

(21) Appl. No.: 18/130,858

(22) Filed: Apr. 4, 2023

(65) Prior Publication Data

US 2023/0238093 A1 Jul. 27, 2023

Related U.S. Application Data

(63) Continuation of application No. 16/297,456, filed on Mar. 8, 2019, now Pat. No. 11,626,192.

(Continued)

(51) Int. Cl.
*G16H 10/60* (2018.01)
*G06Q 40/08* (2012.01)
(Continued)

(52) U.S. Cl.
CPC .............. *G16H 10/60* (2018.01); *G16H 10/40* (2018.01); *G06Q 40/08* (2013.01); *G16H 50/20* (2018.01); *G16H 50/70* (2018.01)

(58) Field of Classification Search
CPC ........ G16H 10/40; G16H 10/60; G16H 50/00; G16H 50/20; G16H 50/70; G06Q 40/08
(Continued)

(56) References Cited

U.S. PATENT DOCUMENTS

| 8,364,500 B2 | 1/2013 | Eisenberger et al. |
| 8,417,533 B2 | 4/2013 | Clawson |

(Continued)

FOREIGN PATENT DOCUMENTS

| CA | 2 777 838 A1 | 4/2011 | |
| CN | 103136629 A * | 6/2013 | ............. G06Q 10/06 |

(Continued)

OTHER PUBLICATIONS

Austin, Tony; The development and comparative evaluation of middleware and database architectures for the implementation of an electronic health care record; University of London, University College London (United Kingdom). ProQuest Dissertations Publishing, 2004. U602810. (Year: 2004).*

(Continued)

*Primary Examiner* — Hiep V Nguyen
(74) *Attorney, Agent, or Firm* — MASCHOFF BRENNAN; Elaine K. Lee

(57) ABSTRACT

The present invention provides systems and methods for use with electronic records, such as Electronic Medical Records (EMRs). A parser engine may receive a stream of Health Level 7 (HL7) messages containing EMR data and, using parsing logic, parse the HL7 messages to identify and extract specified EMR data therefrom. The extracted EMR data may be utilized in determining analytic results data that may be presented, or made available for presentation, to a medical professional or medical staff member, in real time or near real time relative to entry of the EMR data into an EMR system.

22 Claims, 15 Drawing Sheets

Related U.S. Application Data

(60) Provisional application No. 62/701,166, filed on Jul. 20, 2018.

(51) Int. Cl.
    *G16H 10/40*     (2018.01)
    *G16H 50/20*     (2018.01)
    *G16H 50/70*     (2018.01)

(58) Field of Classification Search
    USPC .......................................................... 705/3
    See application file for complete search history.

(56) References Cited

U.S. PATENT DOCUMENTS

| | | | |
|---|---|---|---|
| 8,694,337 | B2 | 4/2014 | Stein et al. |
| 9,092,964 | B1 | 7/2015 | Chan et al. |
| 9,177,106 | B2 | 11/2015 | Smith et al. |
| 10,817,530 | B2 | 10/2020 | Siebel et al. |
| 10,963,795 | B2 | 3/2021 | Bhatt et al. |
| 11,177,041 | B1 | 11/2021 | Sutton et al. |
| 11,482,322 | B1 | 10/2022 | Bhansali et al. |
| 11,501,859 | B1 | 11/2022 | Guillén et al. |
| 11,626,192 | B1 | 4/2023 | Bhansali et al. |
| 2004/0078236 | A1 | 4/2004 | Stoodley et al. |
| 2004/0087864 | A1 | 5/2004 | Grouse |
| 2007/0168223 | A1 | 7/2007 | Fors et al. |
| 2008/0154642 | A1 | 6/2008 | Marble et al. |
| 2008/0255885 | A1* | 10/2008 | Eisenberger ....... G06Q 30/0601 705/3 |
| 2012/0029932 | A1* | 2/2012 | Stein ....................... G16H 15/00 705/2 |
| 2012/0215560 | A1* | 8/2012 | Ofek ....................... G16H 70/20 705/3 |
| 2012/0323588 | A1 | 12/2012 | Kelly et al. |
| 2013/0332194 | A1 | 12/2013 | D'Auria et al. |
| 2014/0236626 | A1 | 8/2014 | Reddy Bynagari |
| 2014/0297302 | A1 | 10/2014 | Vanier et al. |
| 2015/0213224 | A1 | 7/2015 | Amarasingham et al. |
| 2015/0287317 | A1 | 10/2015 | Chan et al. |
| 2015/0339791 | A1 | 11/2015 | Tetteh |
| 2016/0063209 | A1 | 3/2016 | Malaviya |
| 2016/0364544 | A1 | 12/2016 | Das et al. |
| 2017/0006135 | A1* | 1/2017 | Siebel .................... G06Q 10/06 |
| 2017/0061093 | A1 | 3/2017 | Amarasingham et al. |
| 2017/0091388 | A1 | 3/2017 | Zolla et al. |
| 2017/0277732 | A1 | 9/2017 | Dwire et al. |

FOREIGN PATENT DOCUMENTS

| | | |
|---|---|---|
| EP | 2 560 110 A1 | 2/2013 |
| KR | 10-2014-0034618 A | 3/2014 |
| WO | 2014/042942 A1 | 3/2014 |
| WO | 2014/100736 A2 | 6/2014 |
| WO | 2017/091603 A1 | 6/2017 |

OTHER PUBLICATIONS

Guillén et al., U.S. Appl. No. 17/981,370, entitled Patient Callback Tool and Interface, filed Nov. 4, 2022.

Sutton et al., U.S. Appl. No. 17/751,339, entitled Method and System for Cardic Risk Assessment of a Patient Using Historical and Real-Time Data, filed Oct. 26, 2021.

Bhansali et al., U.S. Appl. No. 17/971,534, entitled Patient Trackerboard Tool and Interface, filed Oct. 21, 2022.

Chatterjee et al., "HL7 FHIR with SNOMED-CT to Achieve Semantic and Structural Interoperability in Personal Health Data: A Proof-of-Concept Study," Sensors, 2022, vol. 22, No. 10, 48 pages.

Mochão et al. "IPOscore: An interactive web-based platform for postoperative surgical complications analysis and prediction in the oncology domain," Computer Methods and Programs in Biomedicine, 2022, vol. 219, 15 pages.

Weiss et al. "Machine learning for personalized medicine: predicting primary myocardial infarction from electronic health records," Ai Magazine, 2012, vol. 33, No. 4, pp. 33-45.

Hsia, R.Y., et al., A National Study of the Prevalence of Life-Threatening Diagnoses in Patients with Chest Pain, Jul. 2016, pp. 1029-1032, vol. 176—No. 7, JAMA Internal Medicine.

Antman, E.M., et al., The TIMI Risk Score for Unstable Angina/Non-ST Elevation MI, A Method for Prognostication and Therapeutic Decision Making, American Medical Association, Aug. 16, 2000, pp. 835-842, vol. 284—No. 7, JAMA.

Lagerqvist, B., et al., FRISC score for selection of patients for an early invasive treatment strategy in unstable coronary artery disease, interventional cardiology and surgery, Heart, 2005, pp. 1047-1052, vol. 91—Iss. 8, BMJ Journals.

Six, A.J., et al., Chest pain in the emergency room: value of the HEART score, Netherlands Heart Journal, Jun. 2008, pp. 191-196, vol. 16—No. 6.

Cervellin, G., et al., Diagnostic algorithms for acute coronary syndrome—is one better than another? Annals of Translational Medicine, May 2016, 6 pages, vol. 4—No. 10.

Goodacre, S., et al., The health care burden of acute chest pain, Heart, 2005, pp. 229-230, 91(2).

Goodacre, S., et al., Cost effectiveness of diagnostic strategies for patients with acute, undifferentiated chest pain, Emergency Medicine Journal, 2003, pp. 429-433, 20(5).

Penumetsa, S.C., et al., Outcomes of Patients Admitted for Observation of Chest Pain, Archives of Internal Medicine, May 7, 2012, pp. 873-877, vol. 172—No. 11.

Sharif, S., et al., Does This Patient With Chest Pain Have Acute Coronary Syndrome?, Annals of Emergency Medicine, Jul. 2017, pp. 44-45, vol. 70—No. 1.

Tang, E., et al., Global Registry of Acute Coronary Events (GRACE) hospital discharge risk score accurately predicts long-term mortality post acute coronary syndrome, American Heart Journal, Jan. 2007, pp. 29-35, vol. 153—No. 1, Elsevier.

Than, M., et al., What is an acceptable risk of major adverse cardiac event in chest pain patients soon after discharge from the Emergency Department? A clinical survey, International Journal of Cardiology, 2012, pp. 752-754, vol. 166—No. 3, Elsevier.

Rajkomar, A., et al., Scalable and accurate deep learning with electronic health records, Digital Medicine, May 8, 2018, pp. 1-10, vol. 1—No. 18, nature partner journals.

Alqudah, et al., "Medical data integration using HL7 standards for patient's early identification," PLoS ONE, 2021, vol. 16, No. 12, 16 pages.

* cited by examiner

REAL TIME PARSER FOR USE WITH ELECTRONIC MEDICAL RECORDS

CROSS REFERENCE TO RELATED APPLICATIONS

This application is a continuation of U.S. Non-Provisional application Ser. No. 16/297,456 filed Mar. 8, 2019, which claims benefit of U.S. Provisional Application No. 62/701,166, filed Jul. 20, 2018. The entire content of these applications is hereby incorporated herein by reference.

INTRODUCTION

The present technology relates generally to electronic records, such as Electronic Medical Record (EMR) and Electronic Health Record (EHR) related technology (herein, the term "EMR" is intended to include both EMR and EHR).

Herein, EMR data broadly includes, for example, data associated with medical or health patients, data associated with groups or populations of medical or health patients, data associated with medical or health conditions, status or situations, data associated with medical or health care, etc., whether or not such data is associated with particular medical or health topics or with individual patients.

Some embodiments of the invention provide solutions to technical problems. One technical problem has been providing EMR related analytic data quickly, efficiently and effectively enough to recipients such as doctors and other medical professions and staff. Some embodiments of the invention provide technical solutions to that problem and related problems, such as by allowing current, useful or optimal EMR analytic data to be determined and presented, or made available for presentation, faster than previous systems. For example, in some embodiments, EMR analytic results data is determined and presented, such as displayed, or made available for presentation, in real time or near real time relative to entry of EMR data into an EMR system (which can include, among other things, any system at or into which EMR data is received, logged, recorded or entered, for example), which EMR data is used in determining the analytic results data.

Some embodiments of the invention provide methods and systems that facilitate quickly, efficiently and effectively determining and providing EMR related analytic data. For example, some embodiments of the invention allow EMR related analytic results data to be determined and provided in real time or near real time relative to entry of current EMR data, at an EMR system or site such as at a hospital or medical facility, which current EMR data is used in determination of the analytic results data. More particularly, for example, in some embodiments, EMR related analytic data, such as medical patient related analytic results data, is determined and provided in real time or near real time relative to entry of the most current relevant EMR data, such as current patient data.

In some embodiments, speed and efficiency is facilitated or enabled, for example, by use of a parser engine for parsing and storing particular, needed or selected EMR data from HL7 messages, which EMR data is analyzed to determine EMR analytic results data, such as for various clinical, medical, or health care related needs, requests or uses, which can include, for instance, in connection with many different types of uses, situations, use cases, or use case scenarios. Speed and efficiency may also be facilitated, for example, by use of an optimally designed and managed EMR relational database, which may include an overall tables and views set, and structure or design, and well as structure or design of individual tables and views, including optimization with regard to facilitating methods of embodiments of the invention, including quickly determining EMR analytic results data.

In some embodiments, a parser engine (herein, the terms "parser" and "parser engine" are used interchangeably) is utilized. The parser engine may receive a real time or near real time feed of Health Level 7 (HL7) messages, such as may originate from multiple EMR systems or sites. The parser engine may utilize parser engine logic to identify and extract needed EMR data from the HL7 messages. The parser engine may further direct, or facilitate directing, of storage of the extracted EMR data into an optimally designed and structured relational EMR database. EMR data from the EMR database may be queried, or otherwise obtained, and analyzed to provide needed analytic results data. The analytic results data may be provided in real time or near real time relative to entry of current relevant EMR data, such as, for example, current EMR data needed in determining the analytic results data, or in determining the most complete or optimal analytic results data. The EMR database may include both the most current EMR data as well as historical and chronologically tracked EMR data, and, in some cases, both may be utilized in determining the analytic results data.

While the invention is described with reference to the above drawings, the drawings are intended to be illustrative, and the invention contemplates other embodiments within the spirit of the invention.

DETAILED DESCRIPTION OF EMBODIMENTS OF THE PRESENT INVENTION

The present invention will now be described more fully hereinafter with reference to the accompanying drawings which show, by way of illustration, specific embodiments by which the invention may be practiced. This invention may, however, be embodied in many different forms and should not be construed as limited to the embodiments set forth herein; rather, these embodiments are provided so that this disclosure will be thorough and complete, and will fully convey the scope of the invention to those skilled in the art. Among other things, the present invention may be embodied as devices or methods. Accordingly, the present invention may take the form of an entirely hardware embodiment, an entirely software embodiment, or an embodiment combining software and hardware aspects. The following detailed description is, therefore, not to be taken in a limiting sense.

Throughout the specification and claims, the following terms take the meanings explicitly associated herein, unless the context clearly dictates otherwise. The phrases "in one embodiment," "in an embodiment," and the like, as used herein, does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" includes plural references. The meaning of "in" includes "in" and "on."

It is noted that description herein is not intended as an extensive overview, and as such, concepts may be simplified in the interests of clarity and brevity.

Any process described in this application may be performed in any order and may omit any of the steps in the process. Processes may also be combined with other processes or steps of other processes.

Figure 1:
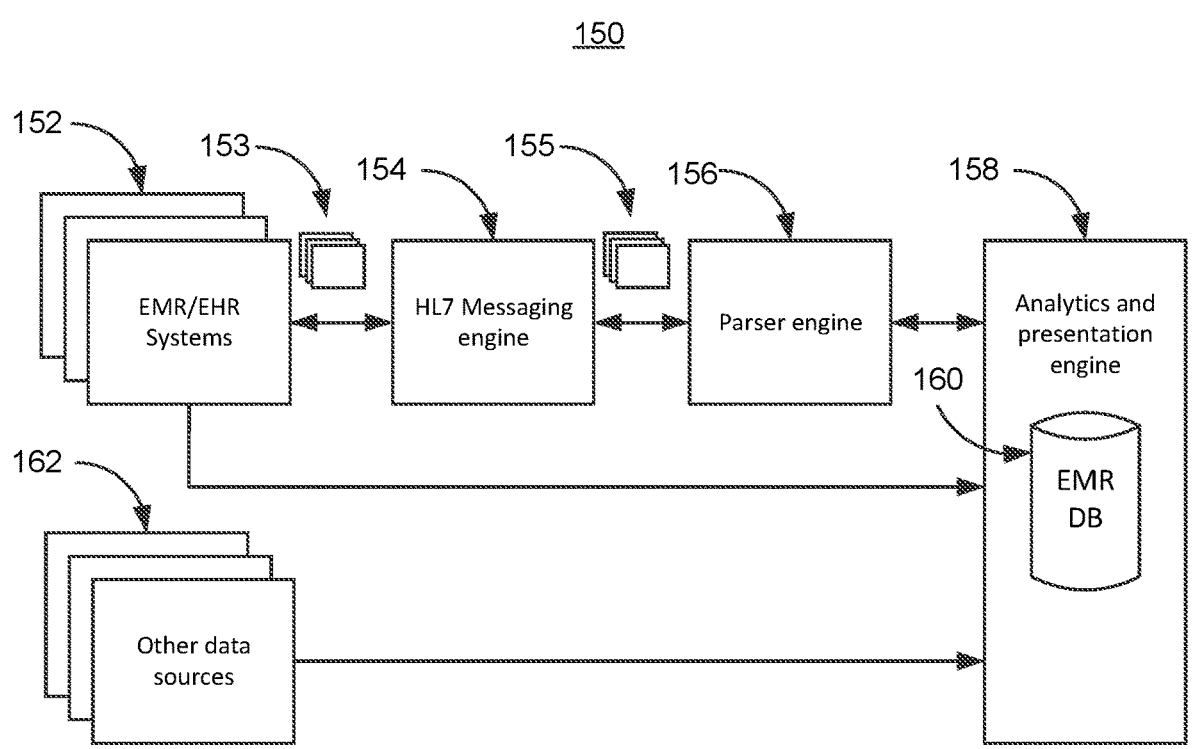
FIG. 1 illustrates a block diagram of an architecture of a system according to some embodiments of the invention, including an HL7 messaging engine and a parser engine.

FIG. 1 illustrates a block diagram of an architecture 150 of a system according to some embodiments of the invention. Depicted are multiple EMR/EHR systems 152, other data sources 162, an HL7 messaging engine 154, a parser engine 156 and an analytics and presentation engine 158. In various embodiments, elements such as the EMR/EHR systems 152, the other data sources 162 and the HL7 messaging engine 154, or portions thereof, may or may not themselves be part of the inventive system. For example, in some embodiments, the parser engine 156 only, or operation thereof, or elements of the parser engine 156, or elements of operation thereof, may constitute an entire inventive system, method, apparatus, architecture, data structure, computer readable media, etc.

It is to be understood that intermediary entities may be present in addition to those depicted, or multiple separate sub-entities of particular entities, and data may be received and sent from such non-depicted intermediaries or sub-entities to, from or within depicted entities, such as from the EMR/EHR systems 152 or the other data sources 162. It is further to be understood that, while a single HL7 messaging engine 154, parser engine 156 and analytics and presentation engine 158 are depicted, each engine can be implemented by or using one or more networks, computers, servers, clients, applications, operating systems, software, hardware, etc., as well as various communications therebetween.

The EMR/EHR systems 152 may be located at or associated with various sites, such as hospitals, medical facilities, doctor's offices, etc. EMR data may be entered, logged, recorded or input at such sites. For example, upon admission of a patient into a hospital, EMR data relating to the patient, e.g. patent's name, patient's demographics, billing information, insurance information, health-related complaint, lab tests ordered for diagnosis, collected vitals or other data, and many other types of data, may be entered, recorded or logged, or collected and entered, recorded or logged, into the hospital's computerized EMR system. In addition, other types of EMR data may be entered.

EMR data entered or logged into the EMR/EHR systems 152 may immediately, such as in real time or near real time, be sent as a stream of data items or HL7 messages 153 to the HL7 messaging engine 154, directly, indirectly or via intermediary entities. Depending on specific circumstances, real time or near real time can be, for example, within seconds or a fraction of a second. In various embodiments, the EMR data sent from the EMR/EHR systems 152 may be in various forms and formats, such as not yet formatted into HL7 messages, partially formatted into HL7 messages, or fully formatted into HL7 messages.

In various embodiments, the HL7 messaging engine 154 may serve a variety of functions, such as relating to formatting, structuring or serializing, or re-formatting, re-structuring or re-serializing or sending, for example, EMR data not in the form of HL7 messages, partial or incompletely formatted or structured HL7 messages, or complete or fully structured HL7 messages. However, in some embodiments, an HL7 engine may be omitted, and HL7 messages may be sent directly or indirectly to the parser engine 156 without first being sent to an HL7 messaging engine 154. Furthermore, in some embodiments, the parser engine 156 alone, or certain elements thereof, may perform all inventive steps or may constitute the entire inventive architecture, method, system, computer readable media, etc. In other embodiments, the parser engine 156 or elements thereof, or other engines or elements other than the parser engine 156, may constitute the entire inventive architecture, method, system, computer readable media, etc.

In some embodiments, the HL7 messaging engine 154 may be implemented, in while or in part, using various tools and designs, such as, for example, a Mirth or Mirth Connect or Nextgen Connect cross-platform HL7 interface engine.

In some embodiments, the HL7 messaging engine 154 plays a role in, for example standardizing, unifying, or otherwise preparing for efficient and fast ingestion by the parser engine 156 of all or part of disparate or variously structured or formatted EMR data or HL7 messages originating from the various EMR/EHR systems 152. This can include, for example, accounting for, labelling or otherwise preparing for ingestion by the parser engine 156 HL7 messages with custom or z-segments specified by particular EMR systems or sites 152. Although embodiments of the invention are described herein generally with reference to HL7 messages, in some embodiments, EMR data or messages other than HL7 messages, or non-medical electronic records, are contemplated and utilized.

As depicted, HL7 messages 155 are sent or streamed from the HL7 messaging engine 154 to the parser engine 156. The parser engine 156 may immediately parse the HL7 messages to identify, locate (such as, within an HL7 message) and extract (which can broadly include copying, duplicating, sending, making use of, etc.) particular HL7 message data, such as using parser logic that may, for example, be embodied in software. The parser engine 156 may direct storage of the extracted HL7 message data in an EMR database 160 of the analytics and presentation engine 158, such as by using relational database interface logic that may, for example, be embodied in software. However, in some embodiments, the directing of the extracted data may be accomplished in whole or in part outside of the parser engine 156, such as in whole or in part by the analytics and presentation engine 158. In some embodiments, the parser engine 156 may direct storage of extracted EMR data as appropriate, optimal or efficient, in tables of the EMR database 160, with logic taking into account the design and structure of the EMR database 160.

The EMR database 160 may be any of various types of data stores and databases, and may or may not be a relational database. In some embodiments, various relational database management systems (RDBMS), tools, applications, programming and programming languages may be used in connection with the EMR database 160 and the directing of extracted data to and from the database 160, such as, for one of many possible examples, SQL (Structured Query Language). The EMR database 160, as well as database management and tools, may be designed and structured, in whole or in part, to accommodate, speed, make more efficient, or optimize its use according to embodiments of the invention.

For various clinical, medical, or health care related needs, requests or uses, the analytics and presentation engine 158 may query the EMR database 160 for needed EMR data. In some embodiments, the EMR database 160 may contain both real-time or near real time data represented as data that has passed through the parser engine 156, and other data, represented as data that has not passed through the parser engine 156. Furthermore, the analytics and presentation engine 158 may use, in determining analytic results data, for example, data from EMR/EHR systems 152 and data from other data sources 162. The utilized data may include data originating as HL7 message data and other data.

The analytics and presentation engine 158 may then analyze or direct analysis of acquired or selected EMR data to determine or generate needed analytical results data, which may be dependent on the use case scenario. The analytical results data may be presented, including made available for presentation, such as display, to, for example, doctors or other medical professionals or medical staff. In determining the analytical result data, the analytics and presentation engine may use logic embodied in software, and may utilize both current, real time or near real time EMR data as well as historical, chronologically tracked EMR data from the EMR database 160. Presentation or display of analytical results data case broadly include presentations or displays that directly or indirectly communicate portions, elements or aspects of the analytical results data, directly or indirectly, or data derived therefrom.

The EMR database 160 may be designed or structured, in whole or in part, to best accommodate its anticipated uses for clinical, medical, or health care related needs, requests or uses according to embodiments of the invention. For example, the tables, views and other structuring elements of the EMR database 160 may be designed and configured to best, quickly, efficiently or optimally enable determination of analytical results data, such as for particular clinical, medical, or health care related needs, requests or uses. For example, in some embodiments, tables that may receive extracted data may include one or more tables with each of patient data, patient encounter data, patient insurance data, insurance provider data, patient codes, clinical event data, clinical lab result data, order data, and others.

Furthermore, in some embodiments, various elements of the overall architecture 150 are designed to function optimally together. For example, aspects of each of various elements, such as the EMR/EHR systems 152, the other data sources 162, the HL7 messaging engine 154, the parser engine 156 and the analytics and presentation engine 158, and logic relating to each, may be designed to operate, communicate or interface quickly, efficiently or optimally with various of the other elements, as well as particular actual, possible, or anticipated clinical, medical, or health care related needs, requests or uses. Aspects of clinical, medical, or health care related needs, requests or uses can include, for instance, the analytic substance of the needed analytic results data (e.g., analytic results data relating to the probability of chest pain being associated with a heart-related event), medical end users and sites, end user or site electronic systems, and many other things. Furthermore, in some embodiments, the HL7 messaging engine 154 and the parser engine 156 design may take into account aspects of each other, as well as aspects of the EMR/EHR systems 152 (such as the formatting and structuring specifics of EMR data or HL7 messages coming from each of them), the other data sources, intermediaries, the design and structure of the analytics and presentation engine 158 and the EMR database 160 (including tables and views structures, for instance), particular actual, possible or anticipated clinical, medical, or health care related needs, requests or uses, and types of analytic results data.

In some embodiments, the design of the overall architecture 150 allows determination and presentation of needed analytic results data for particular clinical, medical, or health care related needs, requests or uses in real time or near real time relative to a time of entry of relevant current EMR data at EMR/EHR systems 152, or relative to a time of sending of the EMR data to the HL7 messaging system 154 or parser engine 156. In some embodiments, the relevant current EMR data can include the most current EMR data needed in determination of the needed analytic results data for a particular use case scenario, which can be used, in some cases, in addition to relevant historical EMR data. In some embodiments, relevant EMR data be determined in whole or in part by the analytics and presentation engine 158. It is to be noted that analytic results data can, in various embodiments, include any desired results data that results from analysis of EMR data.

In general, in various embodiments, various elements of operation of the inventive architecture 150 may operate or produce results faster than previously existing architectures. Such results can include determination and presentation of analytic results data, or other particular results or outcomes, such as parsing of an HL7 message by a parser engine to identify and extract needed or desired EMR data, for example.

In some embodiments, various forms of machine learning and machine learning models and feature sets may be used in various aspects of the architecture 150 and its operation. For example, machine learning may be utilized in building, updating or optimizing, such as periodically or continuously, the HL7 messaging engine 154 or its logic, the parser engine 156 or its logic, or the analytics and presentation engine 158 or its logic, which could include the EMR database 160 format and structure, including overall and individual table and view structures or designs, definitions and configurations, etc. In some embodiments, machine learning techniques are used in connection with current and historical EMR data stored, or other data, in the EMR database 160, potentially among other data.

In some embodiments, data received by, stored in, and potentially merged or integrated in the database 160, such as in tables and views, can include data from various sources. These sources are depicted generally as the EMR/EHR systems 152, as well as the other data sources 162 that can include any sources other than the EMR/EHR systems 152. Furthermore, it is to be understood that data from the EMR/EHR systems 152 and other data sources 162 may be received directly by the database 160, or may first pass through, and potentially be modified or transformed by, one or more intermediaries, such as various intermediary systems or entities. For example, in some cases, data from the EMR/EHR systems 152 may first pass through an intermediary billing-related entity.

Data received by the database 160 from the EMR/EHR systems 152 can include data obtained from HL7 message data or from non-HL7 data. In some embodiments, non-HL7 data does not pass through the HL7 messaging engine 154 or the parser engine 156, prior to being received by the database 160. In some embodiments, non-HL7 message data may be sent from the EMR/EHR systems 152 or the other data sources to EMR database 160 directly or after passing through and potentially being modified or transformed by intermediaries. For example, non-HL7 message data sent by the EMR/EHR systems 152, and not passing through the HL7 messaging engine 154 or the parser engine 156, may include non-real-time or non-near real-time, historical, batch, or periodically or intermittently sent data, where the period or frequency of sending or receipt, whether regular or irregular, can vary greatly. For example, the frequency might be a small fraction of second, one or more seconds, one or more minutes, one or more hours, one or more days, or even longer.

Other data, from the other data sources 162, can include non-public or public source data. The other data can include, for example, billing or insurance-related data. In some embodiments, the other data can include public data that may be used in connection with billing, insurance, health care or medical care providers, or other entities, parties, or aspects of medical or health care, or medical or health care data. For example, in some embodiments, public data may be used in connection with various stored data, such as for data enrichment or supplementation, or in connection with, or to confirm or verify, for example, registrations, licensing or name validation, in connection with providers, insurance companies, billing or billing companies, codes and coding, other parties or entities. For example, in some embodiments, data, such as codes or standards, may be obtained from public databases such as LOINC (Logical Observation Identifiers Names and Codes), or from sources associated with other standards or coding entities, such as National Provider Identifier Standard (NPI) data, for instance.

Figure 2:
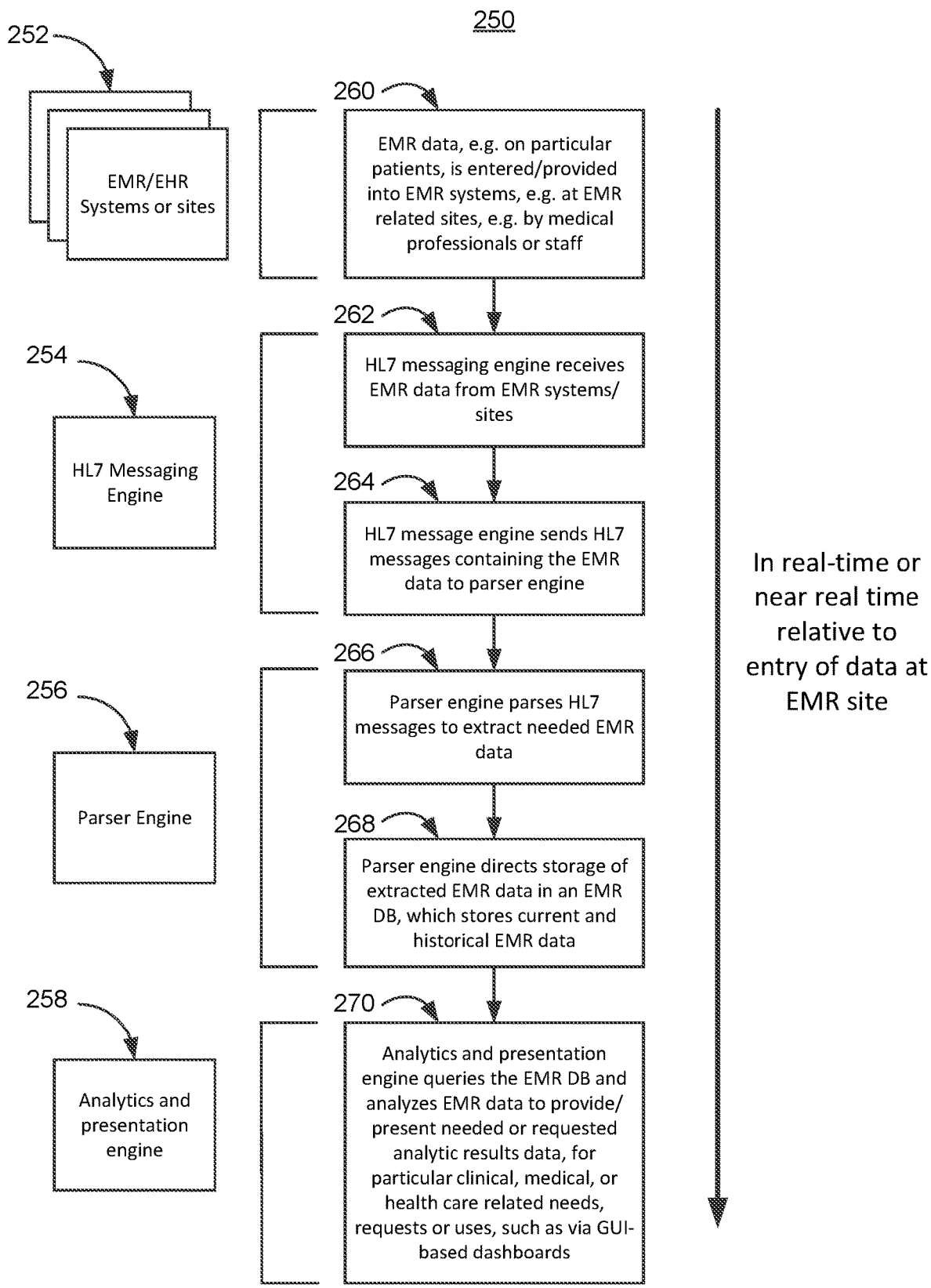
FIG. 2 illustrates a flow diagram of a method according to some embodiments of the invention.

FIG. 2 illustrates a flow diagram of a method 250 according to some embodiments of the invention. At step 260, EMR data, e.g. on particular patients, is entered/provided into EMR systems, e.g. at EMR related sites, e.g. by medical professionals or staff. In some embodiments, this step may be accomplished, in whole or in part, in or at EMR systems 252.

Next, at step 262, an HL7 messaging engine 254 receives EMR data from EMR systems 252, in real time or near real time relative to entry.

Next, at step 264, the HL7 messaging engine 254 sends HL7 messages containing the EMR data to a parser engine 256. In various embodiments, the EMR data sent to the HL7 messaging engine 254 by the EMR systems 252 may be entirely, partially, or not at all structured or formatted as HL7 messages. In some embodiments, the HL7 messaging engine 254 may structure or format the EMR data as HL7 messages, in part or in full, or may re-structure, re-format or re-serialize HL7 messages into re-formatted, re-structured or re-serialized HL7 messages prior to sending to the parser engine 256.

Next, at step 266, the parser engine 256, after receiving the HL7 messages, in real time or near real time relative to entry at the EMR systems 252, directly or indirectly, from the HL7 messaging engine 254, parses the HL7 messages to extract needed EMR data, such as data that is or may be needed for determining and providing analytic results data in various actual, possible or anticipated clinical, medical, or health care related needs, requests or uses. This may include identifying and extracting the EMR data from segments of the HL7 messages. It is noted that, in some embodiments, the parser engine 256 may receive EMR data not in, or partially in, HL7 format or structure, and may itself format, re-format, or re-serialize the data into HL7 format or appropriate, different HL7 format.

Next, at step 268, in real time or near real time relative to entry of the EMR data at the EMR systems 252, the parser engine 256 directs storage of extracted EMR data in an EMR database, which stores current and historical, and in some embodiments chronologically tracked or labelled, EMR data.

Next, at step 270, an analytics and presentation engine 258 queries the EMR database and analyzes EMR data to provide or present needed or requested analytic results data, for particular clinical, medical, or health care related needs, requests or uses, such as via GUI-based dashboards, notifications or other displays or presentation forms (such as text, SMS, social media or other posts or messages, audio, video, 2D or 3D graphics, enhanced or augmented reality presentation forms, or other forms of presentation). In various embodiments, the analytic results data may be displayed or otherwise presented or caused to be presented, made available for presentation or immediate presentation, or made accessible or immediately accessible, such as by end user doctors or other medical professionals or staff. In some embodiments, the analytic results data is presented or made available for presentation securely, privately, confidentially or selectively, or may be available or presented only by use of password, biometric or other authentication, etc.

It is to be noted that, in various embodiments, any, some or all of the depicted steps are accomplished very quickly or more quickly than previous systems and architectures, such as in real time or near real time relative to entry or obtaining of the EMR data at the EMR systems 252, or relative to receipt of the EMR data at the HL7 messaging engine 254, or relative to receipt of the HL7 messages at the parser engine 256, for example.

Figure 3:
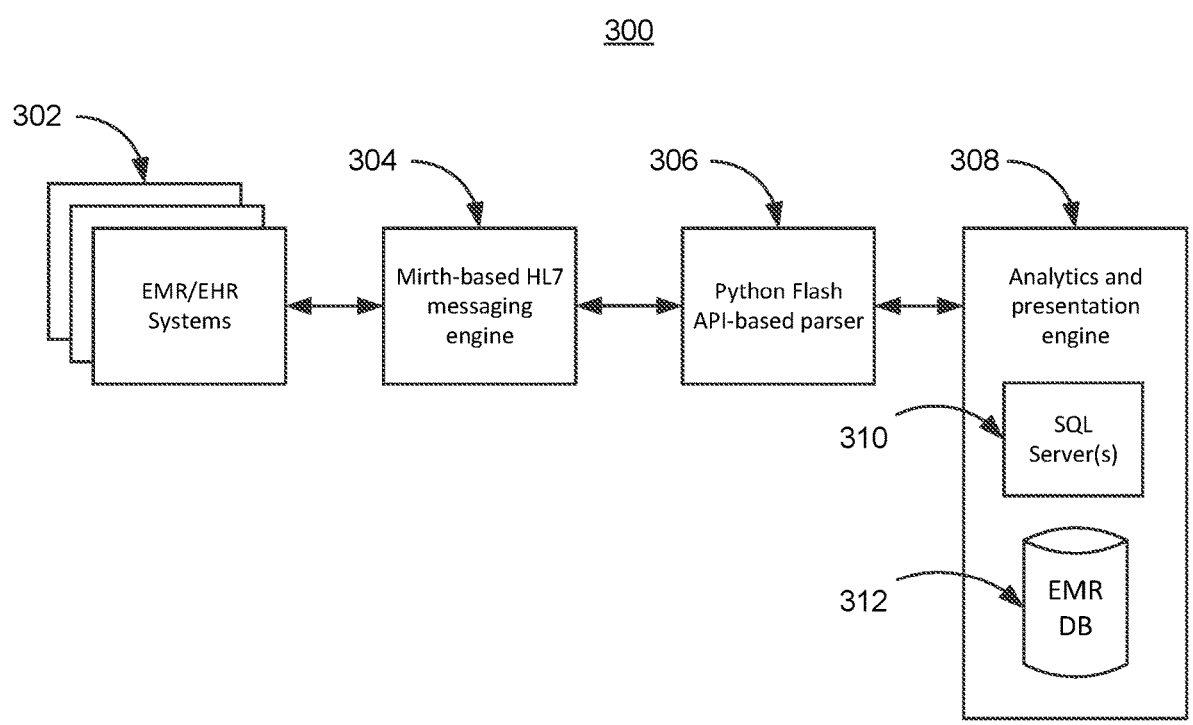
FIG. 3 illustrates a block diagram of an architecture of a system according to some embodiments of the invention, including a Mirth-based HL7 messaging engine and a Python flash API-based parser.

FIG. 3 illustrates a block diagram of an architecture 300 of a system according to some embodiments of the invention, including EMR systems 302, a Mirth-based HL7 messaging engine 304, a Python Flash API-based parser 306 and an analytics and presentation engine 308. In particular, FIG. 3 depicts a specific embodiment of the architecture depicted in FIG. 2 in which the HL7 messaging engine is a Mirth-based HL7 messaging engine 304 (such as based on Mirth Connect or Nextgen Connect), the parser engine is a Python Flash API-based parser 306, and the analytics and presentation engine 308 includes use of one or more SQL servers 310, or the Microsoft SQL Server 2016 platform and temporal tables, such as in relational database management in connection with the EMR database 312, which may be a relational database.

In some embodiments, various aspects of the Mirth-based HL7 messaging engine 304 and the Python Flash API-based parser 306 are selected, designed or configured to operate with, or to operate, interface or communicate efficiently, fast, or optimally with each other or other elements of an inventive architecture. Furthermore, in some embodiments, various aspects of the analytics and presentation engine 308, the EMR database 312, or the EMR systems 302 may also be designed, selected or configured to operate, interface or communicate efficiently, fast or optimally with each other, with the Mirth-based HL7 messaging engine 304, with the Python Flash API-based parser 306, or with other elements of an inventive architecture. Furthermore, other non-depicted elements may be designed to operate optimally with various elements of the inventive architecture, and may incorporate machine learning techniques, models, algorithms or feature sets.

In some embodiments, EMR systems 302 send data streams of HL7 data or messages to the Mirth-based HL7 messaging engine 304, may utilize interface engines in aspects thereof, and may utilize Point-To-Point Tunneling Protocol (PPTP), Minimal Lower Layer Protocol (MLLP) and TCP/IP in communications, including over the Internet. Furthermore, the Mirth-based HL7 messaging engine 304 may include one or more Mirth-based servers, which may send HL7 message receipt or commit acknowledgement messages to the EMR systems 302. Additionally, POST (HTTP) requests may be used in connection with communications between the Mirth-based HL7 messaging engine 304 and the Python Flash API-based parser 306. Furthermore, it is to be noted that, in some embodiments, several separate sets of Mirth-based messaging engines or servers may be utilized and may send and receive HL7 messages as part of the architecture 300.

It is to be noted that, in some embodiments, the depicted architecture 300 allows determination and presentation of analytic results data faster or better than previously existing systems, such as in real time or near real time relative to entry of current EMR data at or into EMR systems 302, which current EMR data is used in determination of the analytic results data.

Figure 4:
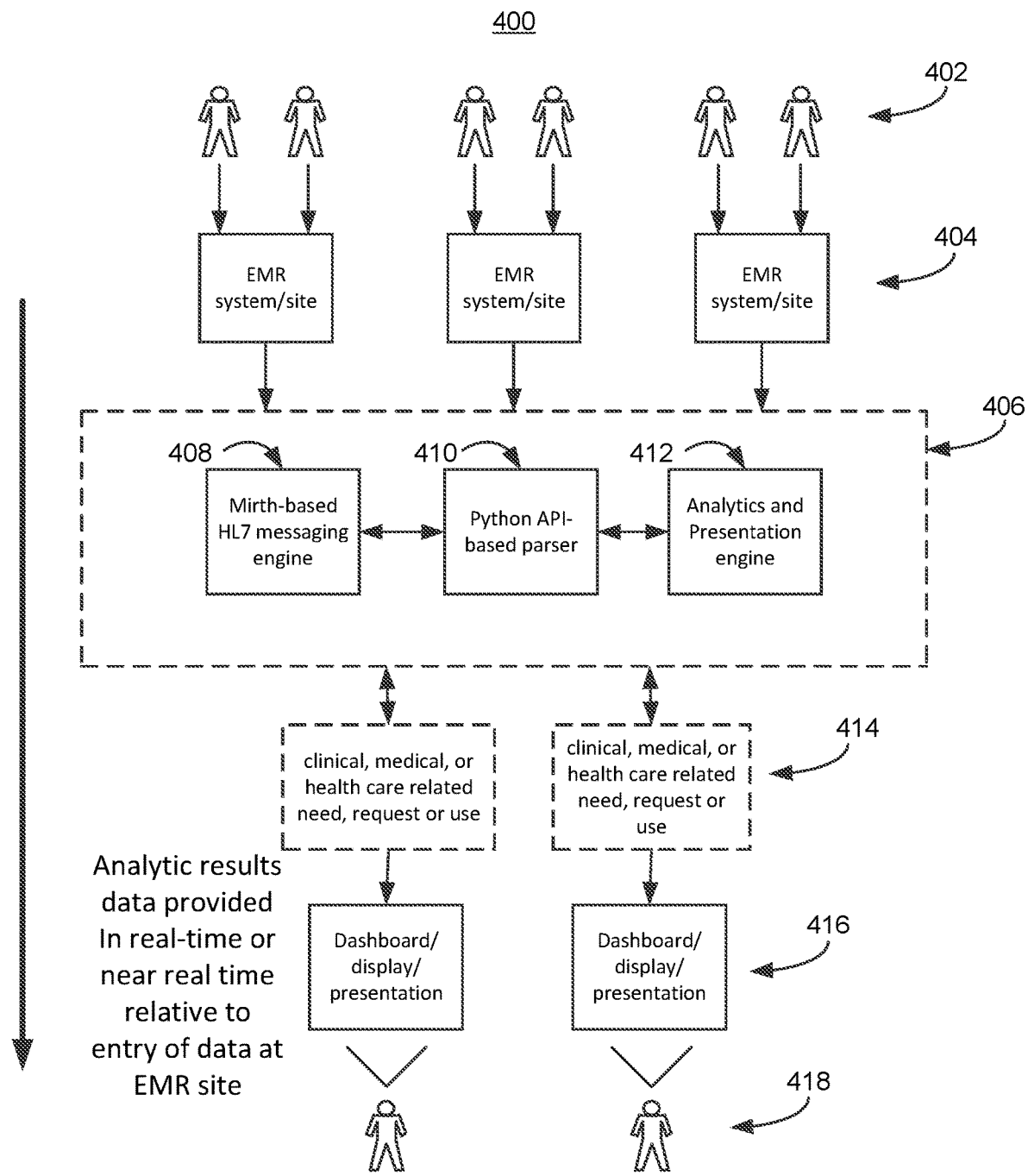
FIG. 4 illustrates a mixed block diagram according to some embodiments of the invention.

FIG. 4 illustrates a mixed block diagram 400 according to some embodiments of the invention. As depicted, various individuals 402 enter or otherwise provide EMR data, such as patient-related data, at various EMR systems or sites 404. It is to be noted that, in some embodiments, EMR data is entered at or obtained by the EMR systems 404 without human entry, such as by other computer systems, APIs, etc.

Each of the EMR systems or sites 404 sends EMR data, directly or indirectly, to an overall system 406 that includes a Mirth-based HL7 messaging engine 408, a Python Flash API-based parser 410, and an analytics and presentation engine 412.

Based on various particular clinical, medical, or health care related needs, requests or uses 414, the system 406 determines and presents dashboards, displays, notifications or other presentations 416 to or for particular end users 418. Clinical, medical, or health care related needs, requests or uses 414 can include, for example, particular doctor or other health care professional or staff needs or requests in connection with particular patient scenarios, etc. The dashboards, displays or other presentations 416 can include or incorporate use of analytic results data determined by the system 400 utilizing the EMR data provided by the EMR systems or sites 404. In some embodiments, the dashboards, displays or other presentations 416 are provided in real time or near time relative to entry of EMR data at the EMR system or site 402, which entered EMR data is used in determining analytic results data used in the dashboards, displays or other presentations 416.

In some embodiments, however, analytic results data may be sent to other computer systems for analysis or other uses, rather than being presented, or presented immediately, to one or more end users.

Figure 5:
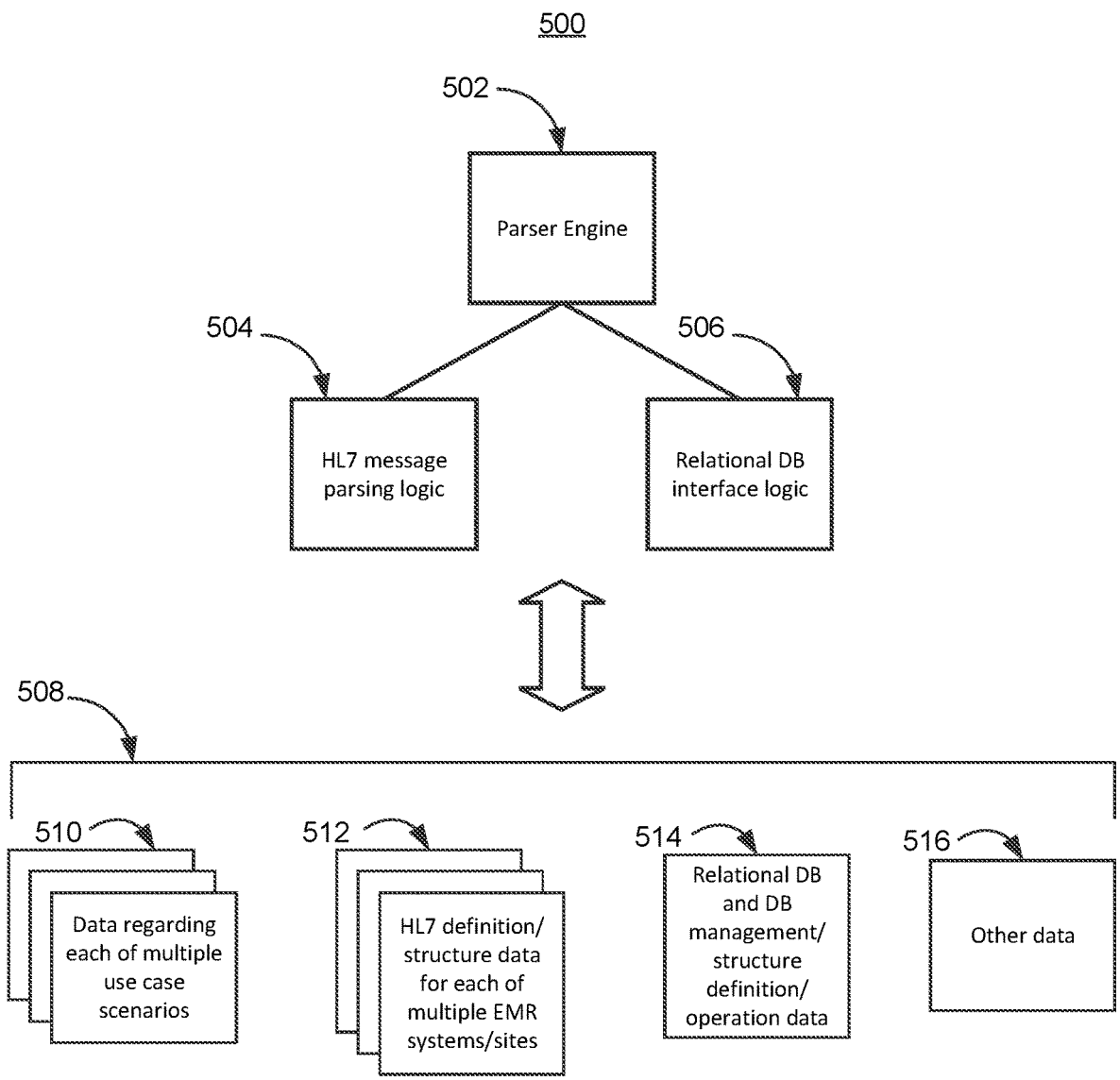
FIG. 5 illustrates a block diagram according to some embodiments of the invention, including HL7 messaging logic and relational database interface logic, of a parser engine.

FIG. 5 illustrates a block diagram 500 according to some embodiments of the invention. A parser engine 502 is depicted, conceptually including elements including HL7 message parsing logic 504 and relational database interface logic 506. As depicted, the parser engine 502 and its elements utilize or work in conjunction with various types of data. As depicted, such data can include, among other types of data, data regarding each of multiple clinical, medical, or health care related needs, requests or uses 510 or types of clinical, medical, or health care related needs, requests or uses. It can further include data regarding HL7 definition(s) or structure(s) for each of multiple EMR systems or sites 512, which can include custom or z-segment segments, etc. Furthermore, it can include relational database and database management definition, structure or operational data 514, which can include, for example, structures or layouts of tables or views, particular table or view definitions, structures and elements, RDBMS languages, applications, hardware elements or other interface specifics, etc., as well as various other data 516.

It is to be noted that, in some embodiments, the parser engine 502 is designed to be able to accommodate and handle disparate sources of data, such as differently formatted or structured EMR data originating from different EMR systems or sites, custom or z-segments of HL7 messages originating from different EMR sites, various different clinical, medical, or health care related needs, requests or uses, various types of analytic results data, etc. For example, operation of the parser engine 502 in parsing, including identifying segments of, particular HL7 messages may incorporate logic relating to the structure of the particular HL7 message, which may in turn depend in part on the originating EMR system or site. In particular, HL7 messages may include z-segments which contain information specified by a particular EMR site or system. In some embodiments, the parser engine 502 (or other engines or elements) includes logic to identify such z-segments and what they contain, in HL7 messages originating from particular EMR sites and systems. Furthermore, in some embodiments, the parser engine 502 operates with, or includes logic to, divide and parse each HL7 message by segment and then operates on a segment type across multiple HL7 messages, which can increase efficiency and speed.

Furthermore, operation of the parser engine 502, such as in selecting particular identified HL7 message data for extraction, may depend part on the set of clinical, medical, or health care related needs, requests or uses that the parser engine 502 is designed to accommodate. Still further, in some embodiments, the parser engine 502 is flexibly designed. For example, the parser engine 502 may be designed to allow frequent parser updating and modification, automatically, by human programmer or developer intervention, via one or more APIs, or otherwise, such as modification to add accommodated EMR systems or site interfaces, or new HL7 message definitions, segments, z-segments, fields or subfields, or to accommodate additional or different clinical, medical, or health care related needs, requests or uses, each of which may require particular stored EMR data, for example.

Figure 6:
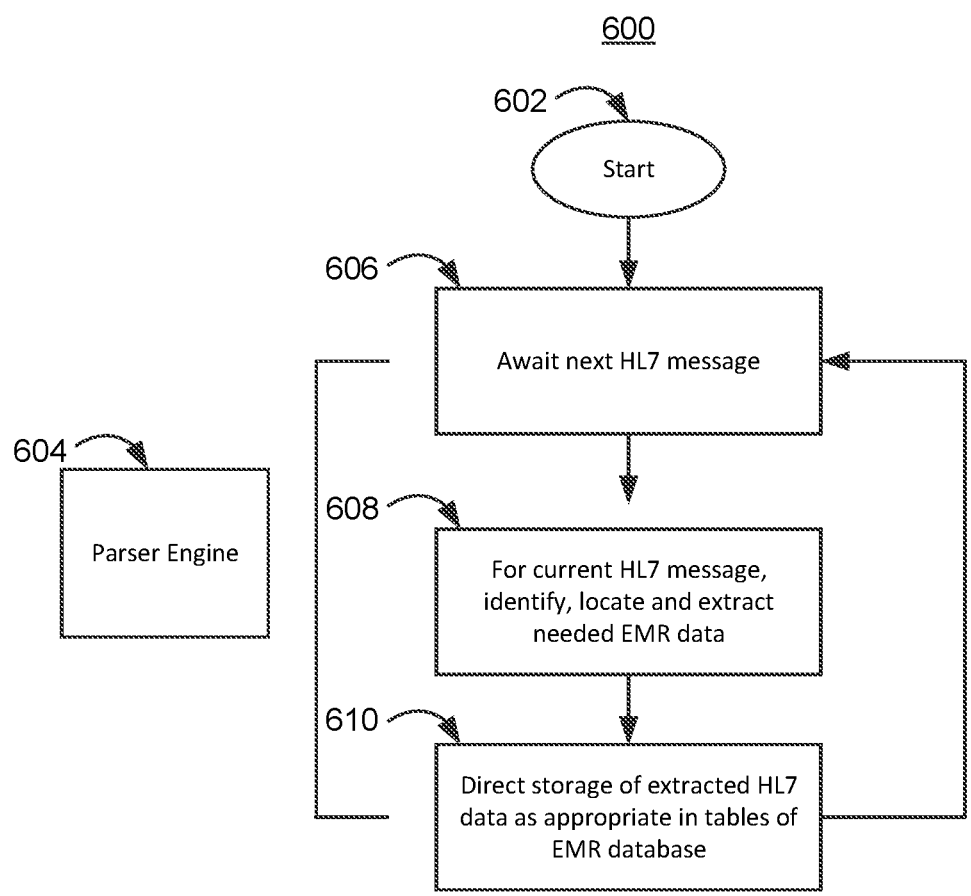
FIG. 6 illustrates a flow diagram of a method relating to parser engine operation according to some embodiments of the invention.

FIG. 6 illustrates a flow diagram of a method 600 relating to parser engine operation according to some embodiments of the invention. In some embodiments, the method 600 may be implemented by a parser engine 604.

After starting at step 602, at step 606 the method 600 awaits the next HL7 message, such as may be included in a real time or near real time stream, flow, feed or series of HL7 messages to the parser engine 604, which, in various embodiments, may come individually or in groups, from one or more EMR systems or intermediaries, at rates of many or even hundreds per second, for instance.

Next, at step 608, for a currently received HL7 message, the parser engine 604 parses the message, including identifying, locating and extracting needed EMR data.

Next, at step 610, the parser engine 604 directs storage of extracted HL7 data as appropriate in tables of an EMR database. In various embodiments, direction of storage of extracted EMR data may be accomplished in whole or in part by systems or elements other than the parser engine 604.

After step 610, the method 600 returns to step 606 and awaits the next HL7 message, which may come a small fraction of a second later than the previous HL7 message, for example.

In some embodiments, through the method 600, over time, a large amount of data may be stored in an EMR database, which data may include historical data over time, originating from multiple EMR systems or sites, which EMR data may be tracked, may include metadata, or may be otherwise stored in such a way as to provide an indication of chronology with respect to the data, such as when it was received by the EMR database, or other chronological information associated with the EMR data or elements or aspects of its substantive contents. Determination of analytical results data may then draw upon this data and its history, chronology, chronological order, chronological periods associated with the data, or chronological metadata. As a simple example, if an admission date and a discharge date for a patient from a hospital is indicated by various EMR data on the patient, a length of stay be calculated therefrom and may be used in determination of, or form part of, analytic results data in some clinical, medical, or health care related needs, requests or uses.

Figure 7:
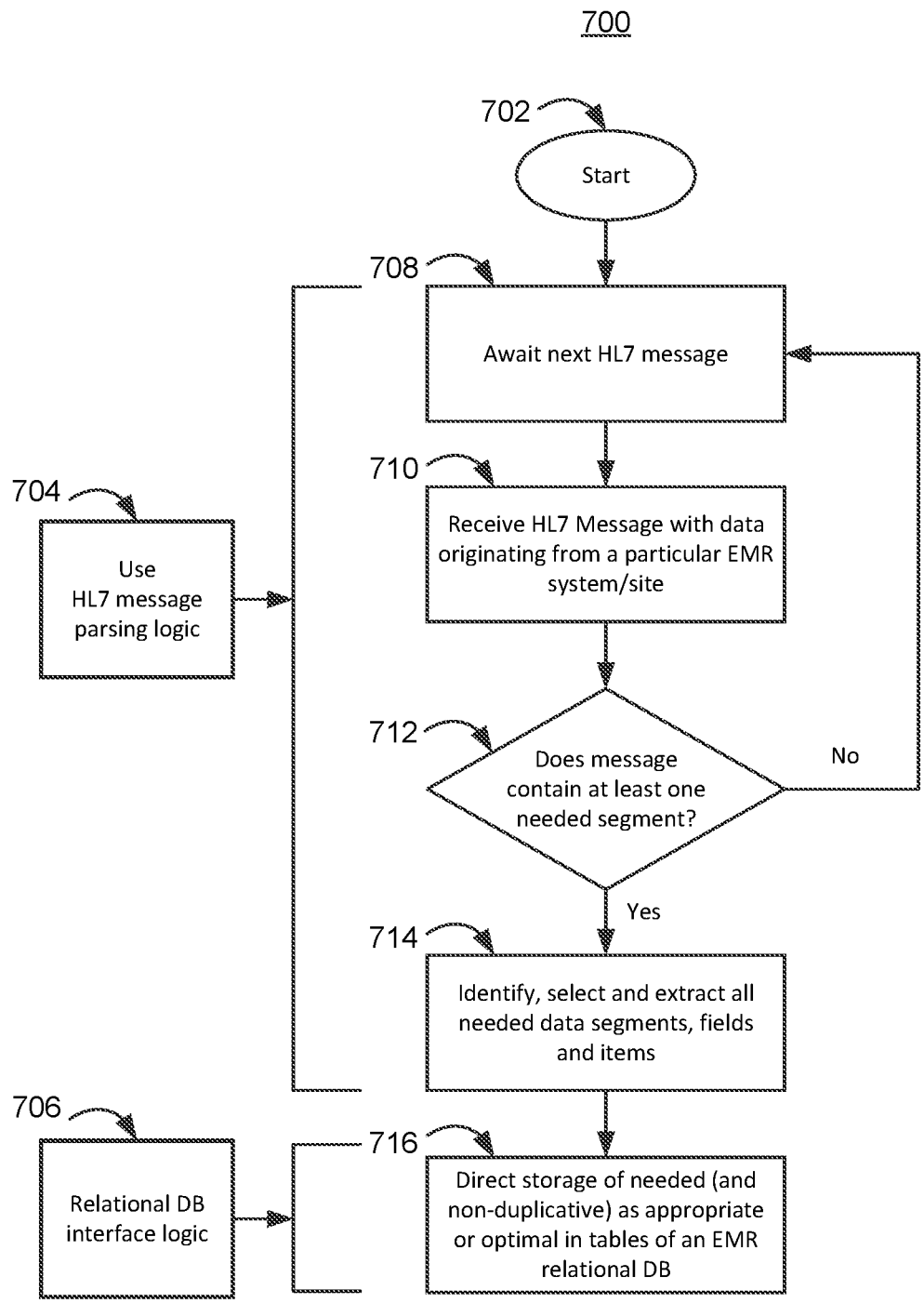
FIG. 7 illustrates a flow diagram of a method relating to parser engine operation according to some embodiments of the invention, including use of HL7 message parsing logic and relational database interface logic.

FIG. 7 illustrates a flow diagram of a method 700 relating to parser engine operation according to some embodiments of the invention, including operation of HL7 message parsing logic 704 and relational database interface logic 706. After starting at step 702, at step 708, the next incoming HL7 message is awaited. Next, at step 710, an HL7 message is received with data originating from a particular EMR system or site. Next, at step 712, it is queried and determined whether the HL7 message includes at least one needed segment. If it does not, no EMR data is extracted, and the method 700 returns to step 708, where the next HL7 message is awaited. If the HL7 message does contain at least one needed segment, then the method 700 proceeds to step 714, where all needed data segments, fields and items are identified, may be selected and are extracted. In some embodiments, all of steps 708, 710, 712 and 714 are implemented utilizing HL7 message parsing logic 704, such as of a parser engine.

At step 716, storage is directed of needed (and non-duplicative) data as appropriate or optimal for storage in tables of an EMR relational database. In some embodiments, step 716 may be implemented utilizing relational database interface logic 706 of a parser engine, although, in other embodiments, some or all of the relational database interface logic may be contained or embodied in elements other than a parser engine or logic thereof.

Figure 8:
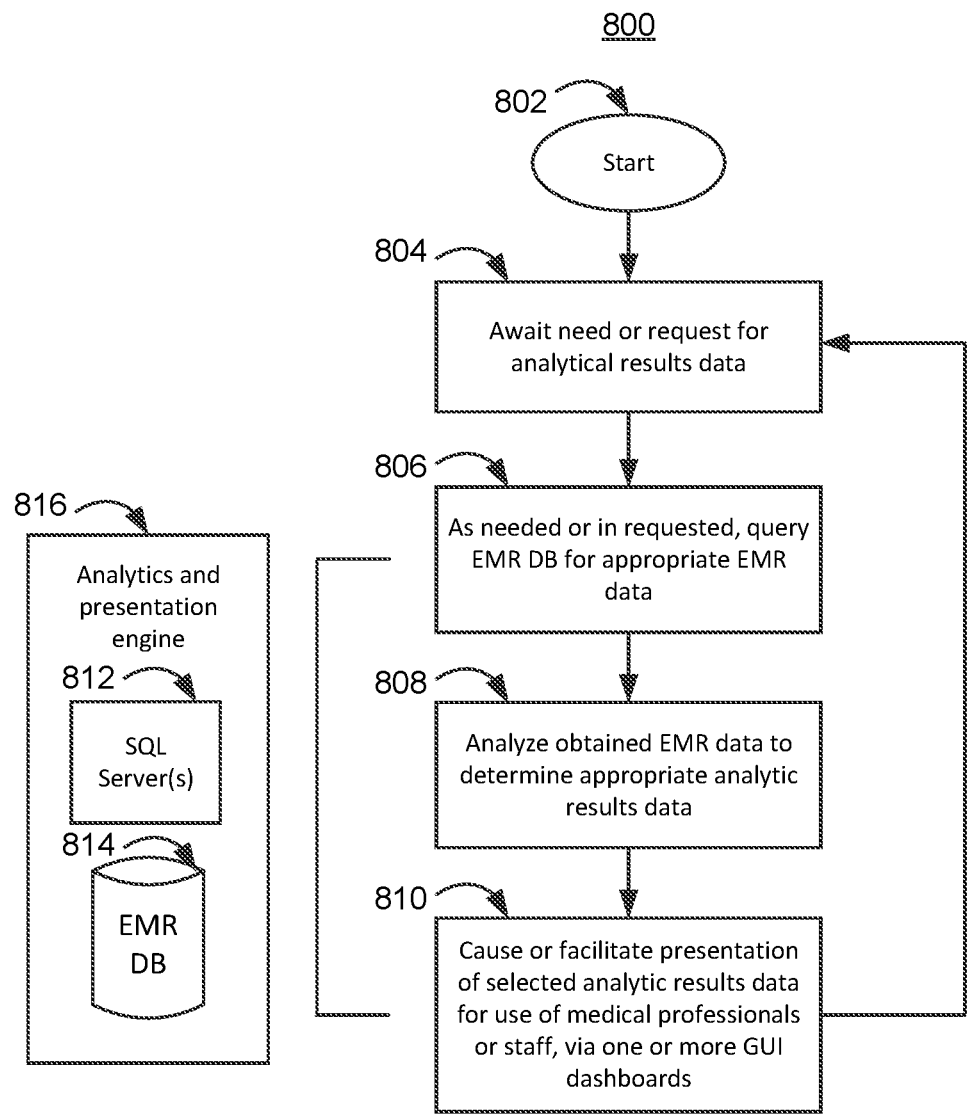
FIG. 8 illustrates a flow diagram of a method relating to analytics and presentation engine operation according to some embodiments of the invention.

FIG. 8 illustrates a flow diagram of a method 800 relating to analytics and presentation engine 816 operation according to some embodiments of the invention. The analytics and presentation engine 816 includes one or more SQL servers 812 and an EMR relational database 814. After starting at step 802, at step 804, the method 800 awaits a need or request for analytical results data. For example, a particular use case scenario may be defined so as to require or call for particular analytic results data at a particular time. Alternatively, a particular request for particular analytic results data may be made and communicated electronically, such as by a medical practitioner or a system of a medical facility, for instance, whether by a human, by a computer system or element communication, automatically, or otherwise.

At step 806, the EMR database 814 is queried for the appropriate EMR data needed to determine the desired or needed analytic results data.

Next, at step 808, the obtained EMR data, potentially along with other data, is analyzed to determine appropriate analytic results data. As a simple example, if the length of stay of a patient at a hospital is desired, obtained EMR data may include data identifying the patient as well as data indicating date of admission and date of discharge of the patient from a hospital, and the simple analysis could include calculation of the length of stay from the admission and discharge dates, for example.

Next, at step 810, the method 800 causes or facilitates presentation of selected analytic results data for use of medical professionals or staff, such as via one or more GUI-based dashboards.

Figure 9:
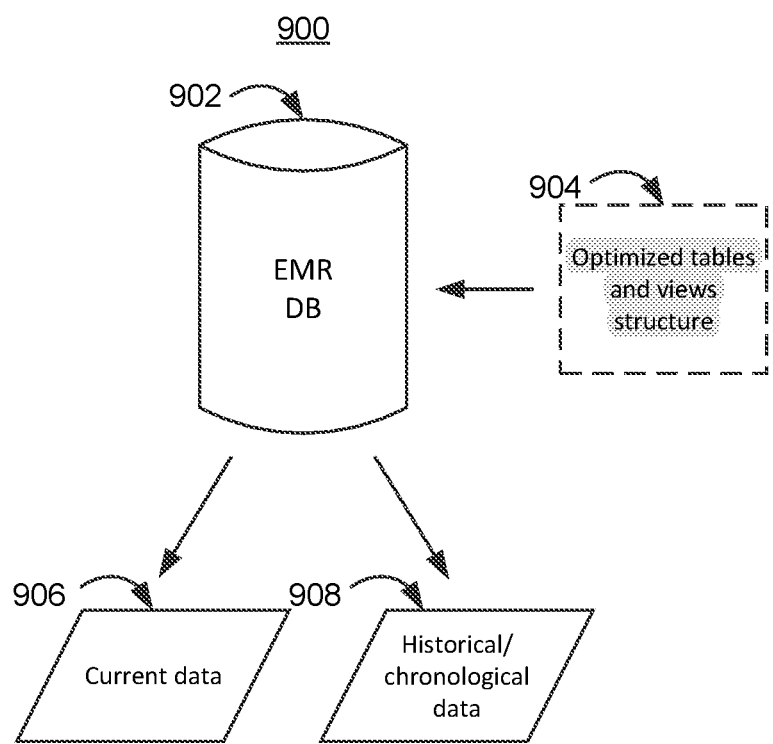
FIG. 9 illustrates a block diagram of an EMR database according to some embodiments of the invention.

FIG. 9 illustrates a block diagram 900 of an EMR database 902 according to some embodiments of the invention. As depicted, the EMR database 902 stores both current data 906 (which may later become historical data) as well as historical/chronological data 908. As depicted, the EMR database 902, which can be a relational database, includes an optimized structure 904, which may include an optimized structure and relationship of multiple tables and views, as well as optimized individual table and view structures, definitions, features, and contents. In some embodiments, the optimization is relative to uses in accordance with methods according to embodiments of the invention. For example, in some embodiments, the database structure optimization 904 may take into account factors relating to aspects or operation of particular EMR systems and sites, such as HL7 message structures, data, and customizations. The database structure optimization 904 may also take into account aspects of an HL7 messaging engine relating to its operation or interfaces with EMR systems and sites or with a parser engine. Furthermore, the database structure optimization 904 may take into account aspects of a parser engine or parser engine logic, such as in connection with optimizing efficiency of such operation. Still further, the database structure optimization 904 may take into account aspects of analytic results and presentation engine structure and operation and related information, including the particulars of actual, anticipated, possible, likely, or sufficiently likely individual clinical, medical, or health care related needs, requests or uses and aspects thereof, including needed EMR data for determining analytic results data in connection with such clinical, medical, or health care related needs, requests or uses.

Figure 10:
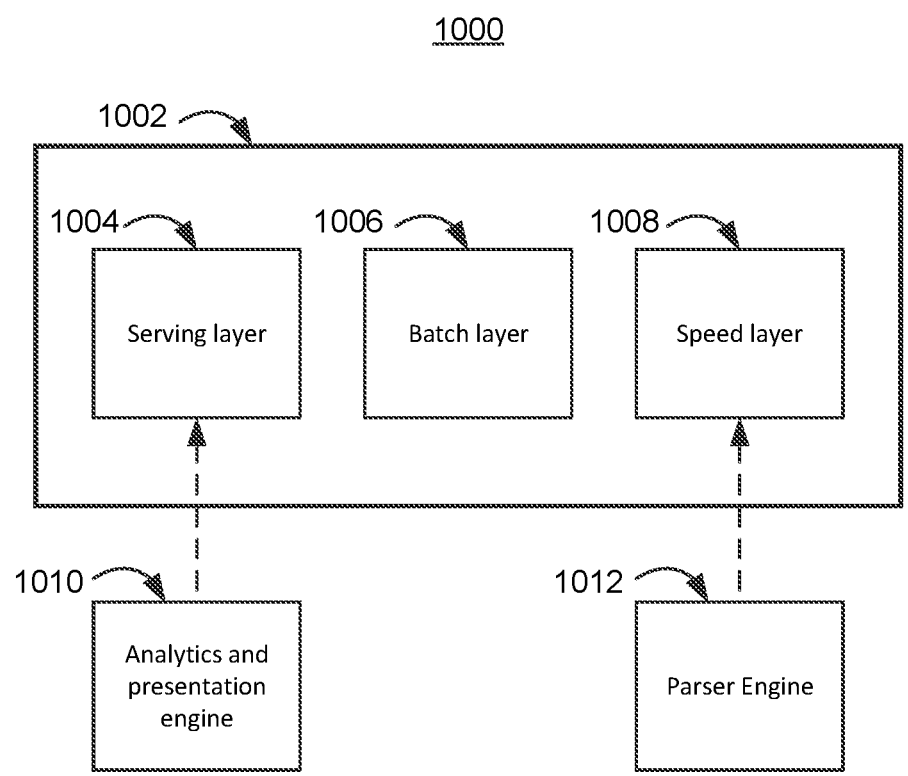
FIG. 10 illustrates a block diagram of an EMR database architecture according to some embodiments of the invention.

FIG. 10 illustrates a block diagram of an EMR database architecture 1000 according to some embodiments of the invention. In some embodiments, architectures, including parser engines, are built modelled on or built on top of lambda architectures or lambda based architectures. Generally lambda architectures are designed to efficiently and quickly handle massive amounts of data by utilizing aspects of both batch and stream processing methods. As depicted, in some embodiments of the invention, a lambda based architecture 1002 is utilized, incorporating a serving layer 1004, a batch layer 1006 and a speed layer 1008. In some embodiments, an analytics and presentation engine 1010 may be, at least in part, associated with, part of, or build on top of the serving layer 1004, whereas a parser engine 1012 may be, at least in part, associated with, part of, or built on top of the speed layer 1008. In some embodiments, utilization of a lambda based architecture allows or helps allow faster and more efficient handling of both current and historical EMR data.

Figure 11:
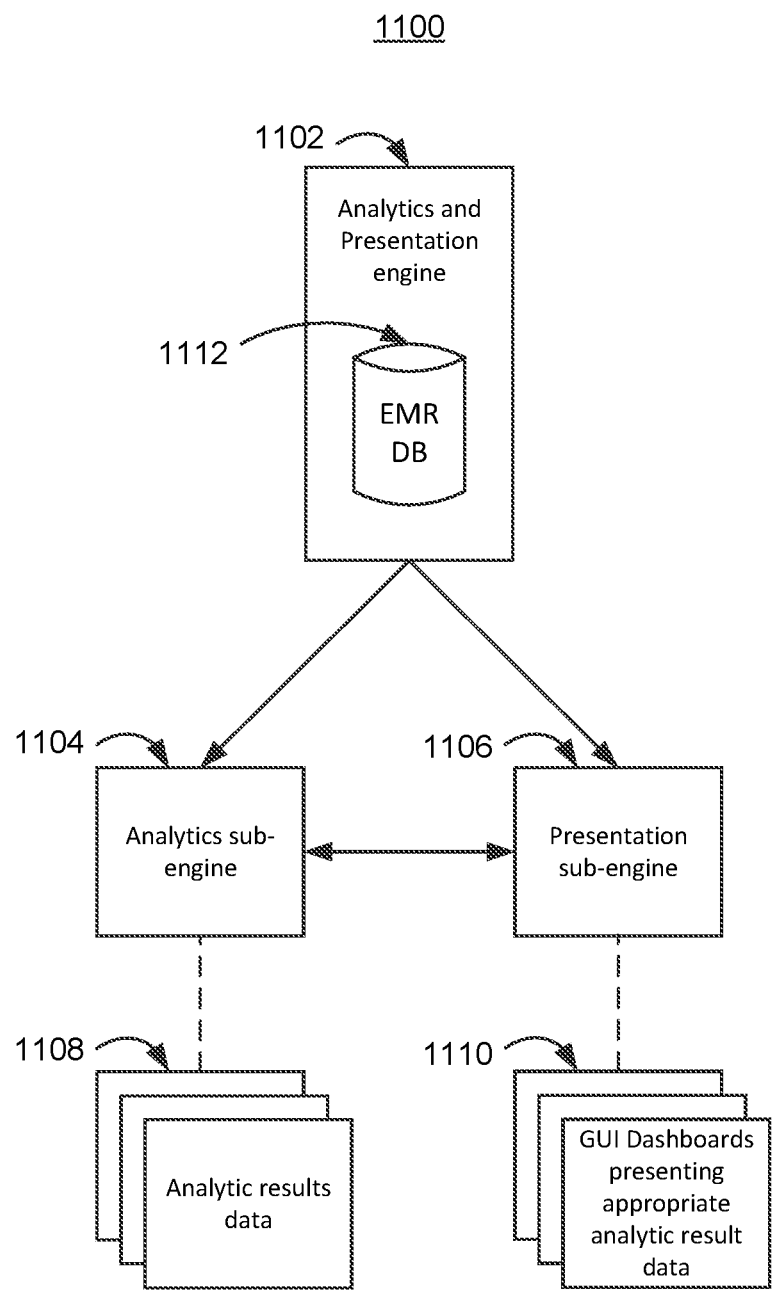
FIG. 11 illustrates a block diagram an analytics and presentation engine, according to some embodiments of the invention.

FIG. 11 illustrates a block diagram 1100 of an analytics and presentation engine 1102, including an EMR database 1112, according to some embodiments of the invention. The engine 1102 includes an analytics sub-engine 1104 and a presentation sub-engine 1106. In the embodiment depicted, the analytics sub-engine 1104 includes logic for, and is used for, determining analytic results data 1108, which may be stored in the EMR database 1112 or elsewhere. The presentation sub-engine 1106 includes logic for, and is used for, presenting or making available analytic results data to end users or systems.

It is to be noted that, in some embodiments, presented analytic results data may be different from, but derived from, initially determined, related analytic results data. As one example, initially determined analytical result data may include a patient's hospital length of stay. Through a GUI based dashboard displaying that data, in some embodiments, a doctor or other medical practitioner may, for instance, request more detailed information about the hospital stay, such as a building or unit in which the patient was placed during the stay. That request may trigger determination of related but different and additional analytic results data for presentation.

Figure 12:
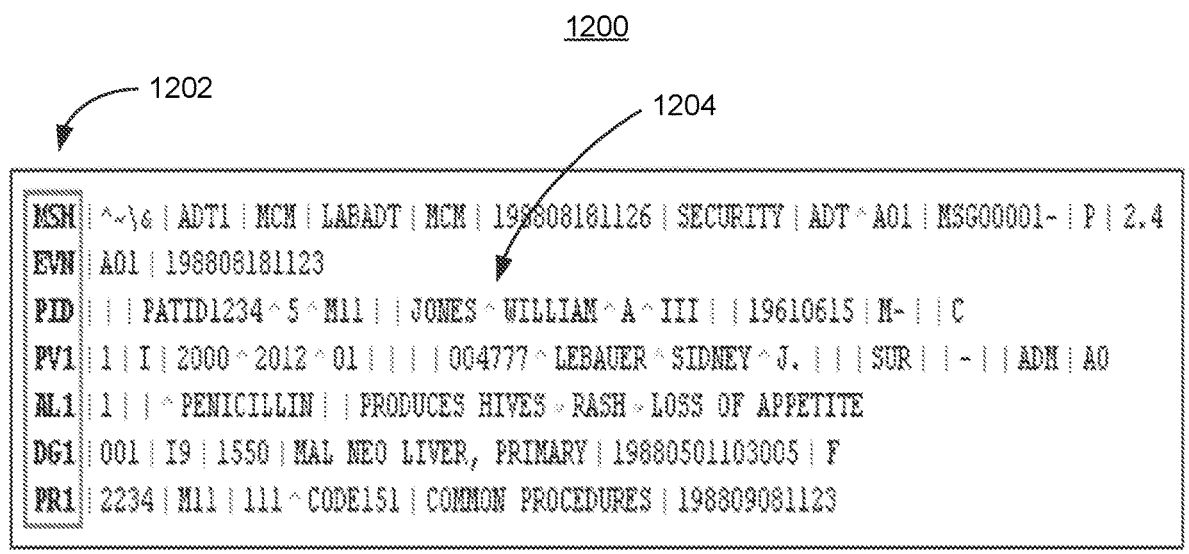
FIG. 12 illustrates a block diagram of elements of an HL7 message according to some embodiments of the present invention.

FIG. 12 illustrates a block diagram of a table 1200 depicting elements of an HL7 message that may be parsed, in some embodiments of the invention. The HL7 message may include segments and identifiers 1202 with particular types of EMR data relating to the patient. Data of each segment is depicted as a row in the table, the first starting with the segment identifier MSH, the second starting with segment identifier EVN, the third starting with the segment identifier PID, the fourth with the segment identifier PV1, etc. In particular, MSH indicates message header, EVN indicates event type, and PID indicates Patient ID, and PV1 indicates a patient visit. Each segment may include a number of fields separated by pipe characters. Furthermore, individual fields may be divided into subfields separated by caret characters.

Figure 13:
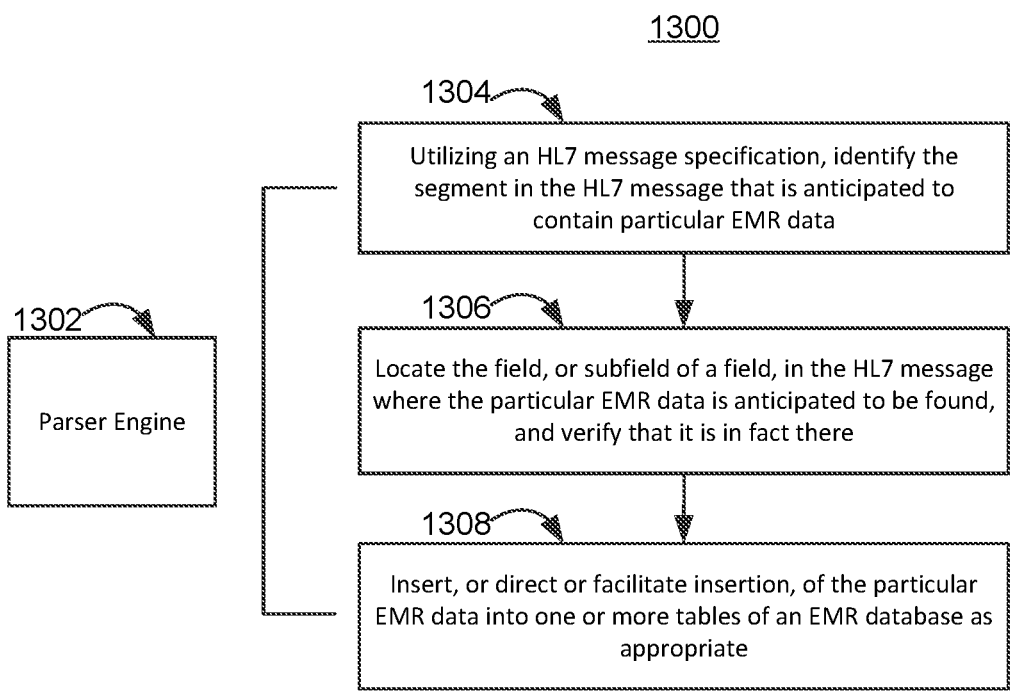
FIG. 13 illustrates flow diagram of a parsing method, according to some embodiments of the invention.

FIG. 13 illustrates a flow diagram of a parsing method 1300, according to some embodiments of the invention, which may be implemented by a parser engine 1302.

At step 1304, utilizing an HL7 message specification, the parser engine 1302 identifies the segment in the HL7 message that is anticipated to contain particular EMR data. Next, at step 1306, the parser engine 1302 locates the field, or subfield of a field, in the HL7 message where the particular EMR data is anticipated to be found, and verifies that it is in fact there. Next, at step 1308, the parser engine 1302 inserts, and/or directs or facilitates insertion, of the particular EMR data into one or more tables of an EMR database as appropriate.

As a specific example or parsing, in some embodiments, a Python Flash API-based parser may parse the following segments:
1. MSH— Message Header
2. PID— Patient Identification
3. PV1— Patient Visit
4. PV2— Patient visit—additional information
5. IN1— Insurance
6. DG1— Diagnosis
7. OBX— Observation
8. OBR— Observation Request
9. ZMA— Z-MedAmerica segment (non HL7 specification)

Furthermore, in some embodiments, the following is a breakdown of different fields that are parsed from the above-listed segments:
1. MSH
   a. Message type
   b. Message number
   c. Site ID
2. PID
   a. MRN
   b. FIN
   c. Date of Birth
   d. Gender
   e. Last Name
   f. First Name
   g. Middle Name
   h. Phone number
3. PV1
   a. Admit datetime
   b. Discharge datetime
   c. Attending Provider Last Name
   d. Attending Provider First Name
   e. Attending Provider Middle Name
   f. Consulting Provider Last Name
   g. Consulting Provider First Name
   h. Consulting Provider Middle Name
   i. Transaction datetime
   j. Encounter class
   k. Encounter type
   l. Medical service
   m. Facility
   n. Building
   o. Nurse or Ambulatory unit
   p. Room or Chair
   q. Bed
   r. Site Name
   s. Discharge Disposition 4. PV2
   a. Pre-Registration datetime
   b. Chief Complaint
5. IN1
   a. Payer Name
   b. Plan Name
   c. Plan Type
   d. Insurance Start datetime
   e. Insurance End datetime
   f. Insurance Member ID
6. DG1
   a. Diagnosis coding method
   b. Diagnosis code
   c. Diagnosis description
   d. Diagnosis datetime
   e. Diagnosis type
7. OBX
   a. Event type
   b. Event value
   c. Event datetime
   d. Event Personnel ID
   e. Dynamic group label ID
8. OBR
   a. Licensed Independent Practitioner first name
   b. Licensed Independent Practitioner last name
   c. Licensed Independent Practitioner middle name
9. ZMA
   a. Order ID
   b. Order description
   c. Order datetime As a particular parsing example, in some embodiments, parsing the patient name from an HL7 message, and updating the parser engine in order to do so if needed, may include the following steps.

If not already present, parsing logic is added to the parser engine to "look for" and identify that segment and field, for example, using appropriate open source tools from the Python Software Foundation. In this example, this may include adding the following code to the parser:

import h17
h=h17·parse(data)
patient name=h·segment('PID')[5]

In various embodiments, this step may not actually be needed, if the parsing logic is already present, or may be accomplished at various times.

Using the specification of the HL7 message and all necessary logic, the parser engine identifies the HL7 message segment in which the patient name should be present.

Next, the parser engine locates the field, or sub-field(s) of a field, where the name can be expected. For example, in the PID segment, the PID.5 field should contain the patient name.

Next, the parser engine checks or verifies the message to ensure that the information is present. In this case, the name 1204, as shown in FIG. 12, is present as expected, and is "William A. Jones III".

Finally, in this example, the parser engine inserts the name data using SQL in the defined table structure of an EMR database using Python— SQL connection, and may utilize SQL stored procedure calls.

In various embodiments of the invention, many different clinical, medical, or health care related needs, requests or uses and analytic results data can be envisioned. Some analytic results data may just require identification and presentation of one or more particular EMR data items relating to a patient, for example. However, some analytic results data may require analysis of varying degrees of complexity, and involving various amounts of EMR data regarding one or more patients, events, transactions, or other things or topics, and may require use of both current (such as real time or near real time relative to entry into an EMR system) and historical/chronological data. One example of a fairly simple analysis, described above, is determining the length of a hospital stay of a patient based on data regarding date of admission and date of discharge of the patient from the facility.

Of course, many different types of data regarding a particular patient can be determined among or from EMR data, some of which may require analysis using either current or historical/chronological data, and some of which may require analysis using both. In addition, some analytic results data may require analysis using EMR data relating to particular transactions or events, or groups, sets or populations of patients, transactions or events, among other things.

However, some analytic results data may require much more EMR data on many patients, or other subjects or topics, as well as, potentially, EMR data on a current patient, including historical and chronological data. For example, some analytic results data may require analysis of a large or huge amount of patient data. As one specific example, suppose that a patient sees a doctor complaining about chest pain. The doctor may desire or require immediate information regarding what the risk is, or what percentage probability or probability range of risk is, that the particular patient is experiencing a cardiac event and/or should be admitted to a hospital immediately. The data utilized in some embodiments of an analysis to provide appropriate analytic results data may be large and varied. For example, it could require analysis of chest pain and cardiac event or non-event data for a large number of patients over a long period of time. Furthermore, it might require data regarding cardiac risk generally, or other topics, even if not specifically individual patient-related. For example, it could require collection of EMR data relating to specific conditions or risks. Furthermore, it could require analysis of EMR data particular to the current complaint of the current patient. Still further, it could involve analysis of historical and chronologically tracked EMR data relating to a large pool of patients as well as the current patient. For example, if increasingly frequent doctor visits by a patient over time for chest pain complaints is associated with a higher risk of a cardiac event, then collection and analysis of data on a large patient pool as well as the current patient on number of such visits over time, and increasing frequency over time, may be relevant and utilized. Still further, the demographics of the current patient, or other characteristics, may be required, as well as associated demographics associated with cardiac risk.

Of course, complex analysis may also require complex and sophisticated analysis logic, such as models, software, modules, algorithms, flows, logic, tools, applications, etc., which are considered part of embodiments of analytic results engines according to some embodiments of the invention, and which may include use of machine learning models or techniques.

Figure 14:
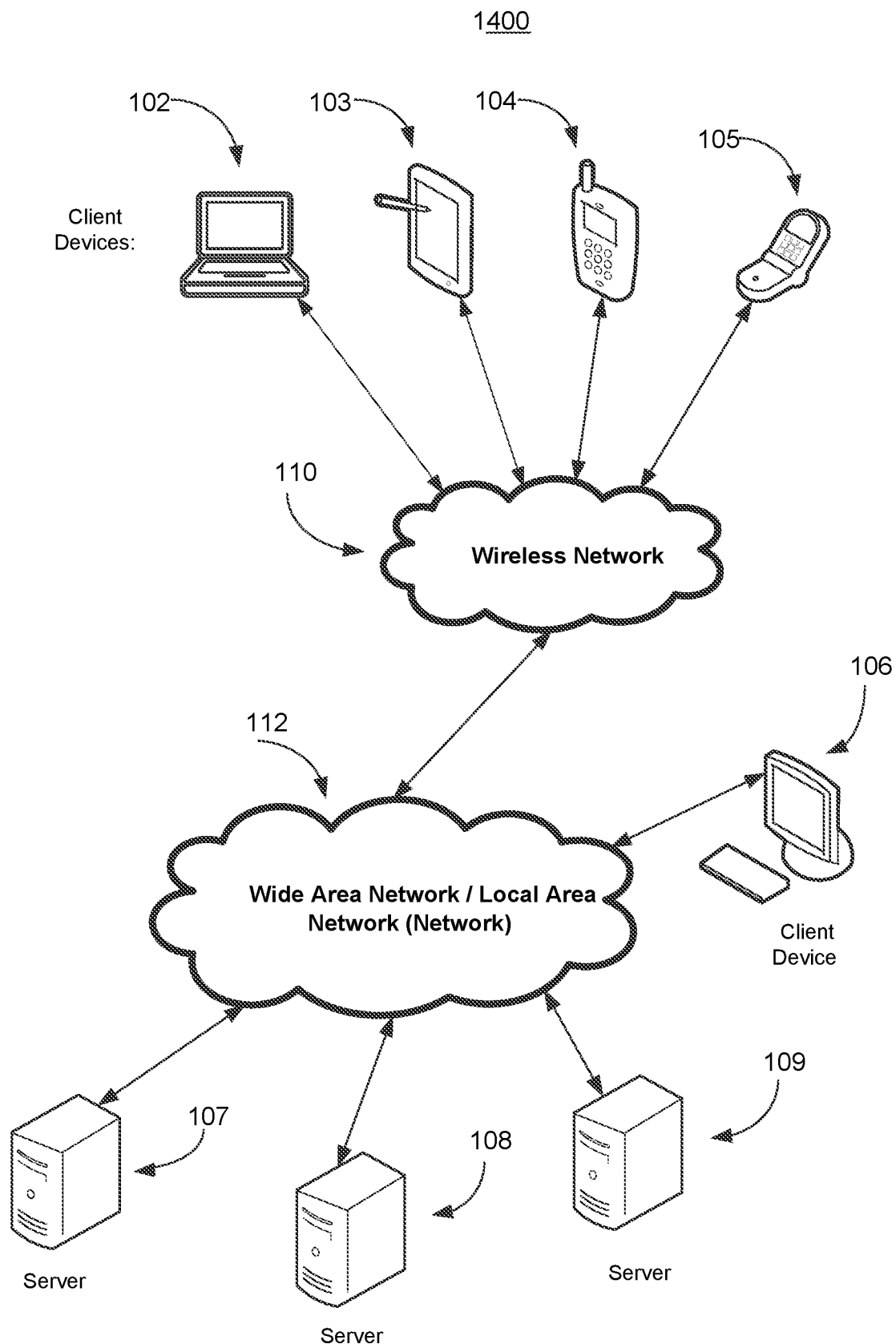
FIG. 14 illustrates a block diagram of a distributed computer system that can implement one or more aspects of an embodiment of the present invention.

FIG. 14 illustrates components of one embodiment of an environment 1400 in which the invention may be practiced. Not all of the components may be required to practice the invention, and variations in the arrangement and type of the components may be made without departing from the spirit or scope of the invention. As shown, the system 1400 includes one or more Local Area Networks ("LANs")/Wide Area Networks ("WANs") 112, one or more wireless networks 110, the Internet, one or more wired or wireless client devices 106, mobile or other wireless client devices 102-106, servers 107-109, and may include or communicate with one or more data stores or databases. Various of the client devices 102-106 may include, for example, desktop computers, laptop computers, set top boxes, tablets, monitors, cell phones, smart phones, devices for interfacing with, or viewing dashboards or analytics relating to, EMR related systems or entities, etc. The servers 107-109 can include, for example, one or more application servers, content servers, search servers, EMR system servers, Mirth-based or other HL7 Messaging servers, Python Flash API-based or other parser engine servers, database servers, database management or SQL servers, etc.

Figure 15:
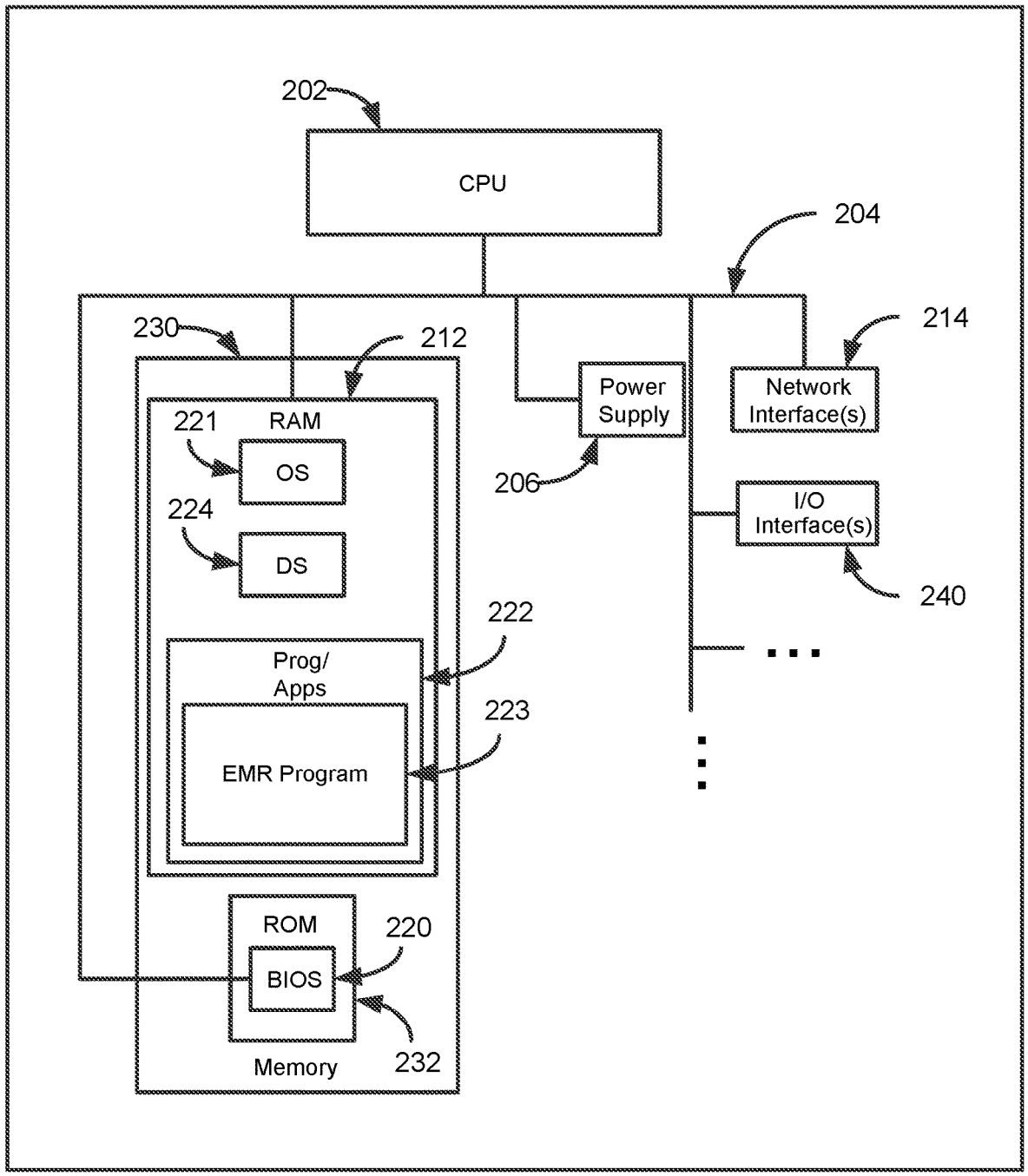
FIG. 15 illustrates a block diagram of an electronic device that can implement one or more aspects of an embodiment of the invention.

FIG. 15 illustrates a block diagram of an electronic device 1500 that can implement one or more aspects of EMR related systems and methods according to embodiments of the invention. Instances of the electronic device 200 may include servers, e.g., servers 107-109, and client devices, e.g., client devices 102-106. In general, the electronic device 200 can include a processor/CPU 202, memory 230, a power supply 206, and input/output (I/O) components/devices 240, e.g., microphones, speakers, displays, touchscreens, keyboards, mice, keypads, microscopes, GPS components, etc., which may be operable, for example, to provide graphical user interfaces, dashboards, etc.

A user may provide input via a touchscreen of an electronic device 200. A touchscreen may determine whether a user is providing input by, for example, determining whether the user is touching the touchscreen with a part of the user's body such as his or her fingers. The electronic device 200 can also include a communications bus 204 that connects the aforementioned elements of the electronic device 200. Network interfaces 214 can include a receiver and a transmitter (or transceiver), and one or more antennas for wireless communications.

The processor 202 can include one or more of any type of processing device, e.g., a Central Processing Unit (CPU), and a Graphics Processing Unit (GPU). Also, for example, the processor can be central processing logic, or other logic, may include hardware, firmware, software, or combinations thereof, to perform one or more functions or actions, or to cause one or more functions or actions from one or more other components. Also, based on a desired application or need, central processing logic, or other logic, may include, for example, a software controlled microprocessor, discrete logic, e.g., an Application Specific Integrated Circuit (ASIC), a programmable/programmed logic device, memory device containing instructions, etc., or combinatorial logic embodied in hardware. Furthermore, logic may also be fully embodied as software.

The memory 230, which can include Random Access Memory (RAM) 212 and Read Only Memory (ROM) 232, can be enabled by one or more of any type of memory device, e.g., a primary (directly accessible by the CPU) or secondary (indirectly accessible by the CPU) storage device (e.g., flash memory, magnetic disk, optical disk, and the like). The ROM 232 can also include Basic Input/Output System (BIOS) 220 of the electronic device.

The RAM can include an operating system 221, data storage 224, which may include one or more databases, and programs and/or applications 222 and an EMR program 223. The EMR program 223 is intended to broadly include all programming, applications, algorithms, software and other tools necessary to implement or facilitate methods and systems according to embodiments of the invention. Elements of the EMR program 223 program may exist on a single server computer or be distributed among multiple computers, servers, devices or entities, or sites.

The power supply 206 contains one or more power components, and facilitates supply and management of power to the electronic device 200.

The input/output components, including Input/Output (I/O) interfaces 240, can include, for example, any interfaces for facilitating communication between any components of the electronic device 200, components of external devices (e.g., components of other devices of the network or system 100), and end users. For example, such components can include a network card that may be an integration of a receiver, a transmitter, a transceiver, and one or more input/output interfaces. A network card, for example, can facilitate wired or wireless communication with other devices of a network. In cases of wireless communication, an antenna can facilitate such communication. Also, some of the input/output interfaces 240 and the bus 204 can facilitate communication between components of the electronic device 200, and in an example can ease processing performed by the processor 202.

Where the electronic device 200 is a server, it can include a computing device that can be capable of sending or receiving signals, e.g., via a wired or wireless network, or may be capable of processing or storing signals, e.g., in memory as physical memory states. The server may be an application server that includes a configuration to provide one or more applications.

Any computing device capable of sending, receiving, and processing data over a wired and/or a wireless network may act as a server, such as in facilitating aspects of implementations of EMR or other related systems and methods according to embodiments of the invention. Devices acting as a server may include devices such as dedicated rack-mounted servers, desktop computers, laptop computers, set top boxes, integrated devices combining one or more of the preceding devices, etc.

Servers may vary widely in configuration and capabilities, but they generally include one or more central processing units, memory, mass data storage, a power supply, wired or wireless network interfaces, input/output interfaces, and an operating system such as Windows Server, Mac OS X, Unix, Linux, FreeBSD, and the like.

A server may include, for example, a device that is configured, or includes a configuration, to provide data or content via one or more networks to another device, such as in facilitating aspects of an example EMR systems and methods according to embodiments of the invention. One or more servers may, for example, be used in hosting a Web site, such as the web site www.microsoft.com. One or more servers may host a variety of sites, such as, for example, business sites, informational sites, social networking sites, educational sites, wilds, financial sites, government sites, personal sites, and the like.

Servers may also, for example, provide a variety of services, such as Web services, third-party services, audio services, video services, email services, HTTP or HTTPS services, Instant Messaging (IM) services, Short Message Service (SMS) services, Multimedia Messaging Service (MMS) services, File Transfer Protocol (FTP) services, Voice Over IP (VOIP) services, calendaring services, phone services, and the like, all of which may work in conjunction with example aspects of EMR systems and methods according to embodiments of the invention. Content may include, for example, text, images, audio, video, and the like.

In example aspects of EMR systems and methods according to embodiments of the invention, client devices may include, for example, any computing device capable of sending and receiving data over a wired and/or a wireless network. Such client devices may include desktop computers as well as portable devices such as cellular telephones, smart phones, display pagers, Radio Frequency (RF) devices, Infrared (IR) devices, Personal Digital Assistants (PDAs), handheld computers, GPS-enabled devices tablet computers, monitors, sensor-equipped devices, laptop computers, set top boxes, wearable computers, integrated devices combining one or more of the preceding devices, and the like.

Client devices may range widely in terms of capabilities and features. For example, a cell phone, smart phone or tablet may have a numeric keypad and a few lines of monochrome Liquid-Crystal Display (LCD) display on which only text may be displayed. In another example, a Web-enabled client device may have a physical or virtual keyboard, data storage (such as flash memory or SD cards), accelerometers, gyroscopes, GPS or other location-aware capability, and a 2D or 3D touch-sensitive color screen on which both text and graphics may be displayed.

Client devices, such as client devices 102-106, for example, as may be used in example EMR systems and methods according to embodiments of the invention, may run a variety of operating systems, including personal computer operating systems such as Windows, iOS or Linux, and mobile operating systems such as iOS, Android, Windows Mobile, and the like. Client devices may be used to run one or more applications that are configured to send or receive data from another computing device. Client applications may provide and receive textual content, multimedia information, and the like. Client applications may perform actions such as viewing or interacting with analytics or dashboards, interacting with medical, patient-related, hospital or medical facility-related, EMR or EMR-related entities or systems, browsing webpages, using a web search engine, interacting with various apps stored on a smart phone, sending and receiving messages via email, SMS, or MMS, playing games, receiving advertising, watching locally stored or streamed video, or participating in social networks.

In example aspects of EMR systems and methods according to embodiments of the invention, one or more networks, such as networks 110 or 112, for example, may couple servers and client devices with other computing devices, including through wireless network to client devices. A network may be enabled to employ any form of computer readable media for communicating information from one electronic device to another. A network may include the Internet in addition to Local Area Networks (LANs), Wide Area Networks (WANs), direct connections, such as through a Universal Serial Bus (USB) port, other forms of computer-readable media, or any combination thereof. On an interconnected set of LANs, including those based on differing architectures and protocols, a router acts as a link between LANs, enabling data to be sent from one to another.

Communication links within LANs may include twisted wire pair or coaxial cable, while communication links between networks may utilize analog telephone lines, cable lines, optical lines, full or fractional dedicated digital lines including T1, T2, T3, and T4, Integrated Services Digital Networks (ISDNs), Digital Subscriber Lines (DSLs), wireless links including satellite links, optic fiber links, or other communications links known to those skilled in the art. Furthermore, remote computers and other related electronic devices could be remotely connected to either LANs or WANs via a modem and a telephone link.

A wireless network, such as wireless network 110, as in example EMR systems and methods according to embodiments of the invention, may couple devices with a network. A wireless network may employ stand-alone ad-hoc networks, mesh networks, Wireless LAN (WLAN) networks, cellular networks, and the like.

A wireless network may further include an autonomous system of terminals, gateways, routers, or the like connected by wireless radio links, or the like. These connectors may be configured to move freely and randomly and organize themselves arbitrarily, such that the topology of wireless network may change rapidly. A wireless network may further employ a plurality of access technologies including 2nd (2G), 3rd (3G), 4th (4G) generation, Long Term Evolution (LTE) radio access for cellular systems, WLAN, Wireless Router (WR) mesh, and the like. Access technologies such as 2G, 2.5G, 3G, 4G, and future access networks may enable wide area coverage for client devices, such as client devices with various degrees of mobility. For example, a wireless network may enable a radio connection through a radio network access technology such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LTE Advanced, Wideband Code Division Multiple Access (WCDMA), Bluetooth, 802.11b/g/n, and the like. A wireless network may include virtually any wireless communication mechanism by which information may travel between client devices and another computing device, network, and the like.

Internet Protocol (IP) may be used for transmitting data communication packets over a network of participating digital communication networks, and may include protocols such as TCP/IP, UDP, DECnet, NetBEUI, IPX, Appletalk, and the like. Versions of the Internet Protocol include IPv4 and IPv6. The Internet includes local area networks (LANs), Wide Area Networks (WANs), wireless networks, and long haul public networks that may allow packets to be communicated between the local area networks. The packets may be transmitted between nodes in the network to sites each of which has a unique local network address. A data communication packet may be sent through the Internet from a user site via an access node connected to the Internet. The packet may be forwarded through the network nodes to any target site connected to the network provided that the site address of the target site is included in a header of the packet. Each packet communicated over the Internet may be routed via a path determined by gateways and servers that switch the packet according to the target address and the availability of a network path to connect to the target site.

The header of the packet may include, for example, the source port (16 bits), destination port (16 bits), sequence number (32 bits), acknowledgement number (32 bits), data offset (4 bits), reserved (6 bits), checksum (16 bits), urgent pointer (16 bits), options (variable number of bits in multiple of 8 bits in length), padding (may be composed of all zeros and includes a number of bits such that the header ends on a 32 bit boundary). The number of bits for each of the above may also be higher or lower.

A "content delivery network" or "content distribution network" (CDN), as may be used in example EMR systems and methods according to embodiments of the invention, generally refers to a distributed computer system that comprises a collection of autonomous computers linked by a network or networks, together with the software, systems, protocols and techniques designed to facilitate various services, such as the storage, caching, or transmission of content, streaming media and applications on behalf of content providers. Such services may make use of ancillary technologies including, but not limited to, "cloud computing," distributed storage, DNS request handling, provisioning, data monitoring and reporting, content targeting, personalization, and business intelligence. A CDN may also enable an entity to operate and/or manage a third party's Web site infrastructure, in whole or in part, on the third party's behalf.

A Peer-to-Peer (or P2P) computer network relies primarily on the computing power and bandwidth of the participants in the network rather than concentrating it in a given set of dedicated servers. P2P networks are typically used for connecting nodes via largely ad hoc connections. A pure peer-to-peer network does not have a notion of clients or servers, but only equal peer nodes that simultaneously function as both "clients" and "servers" to the other nodes on the network.

One embodiment of the present invention includes systems, methods, and a non-transitory computer readable storage medium or media tangibly storing computer program logic capable of being executed by a computer processor.

While certain illustrative embodiments are described herein, it should be understood that those embodiments are presented by way of example only, and not limitation. While the embodiments have been particularly shown and described, it will be understood that various changes in form and details may be made. Although various embodiments have been described as having particular features and/or combinations of components, other embodiments are possible having a combination of any features and/or components from any of embodiments as discussed above.

What is claimed is:

1. A computer-implemented system for use with Electronic Medical Records (EMRs), the system comprising:
    a parser engine configured to:
        receive, in real time or near real time relative to entry of current visit EMR data into at least one EMR system by at least one user during a current medical visit, health care data messages including the current visit EMR data; and
        using parsing logic, parse, in real time or near real time relative to entry of the current visit EMR data, the health care data messages to identify and extract specified EMR data comprising patient clinical data obtained during the current medical visit wherein the parsing logic comprises logic to identify particular segments within the health care data messages corresponding to the specified EMR data, and particular fields within the particular segments;
    a database system configured to, in real time or near real time relative to entry of the current visit EMR data, receive and store the extracted specified EMR data, the database system comprising structuring elements including views and tables configured to enable determination of specified analytic results data including a risk assessment of an Emergency Department (ED) visit by the one or more patients occurring within a specified time period, based on a particular analytical use case related to the current visit; and
    an analytics and presentation engine configured to:
        obtain, from the database system, in real time or near real time relative to entry of the current visit EMR data, particular health care data required to determine the specified analytic results data, wherein the particular health care data has passed through the parser engine and comprises particular fields and segments corresponding to at least some of the specified EMR data; and
        analyze, in real time or near real time relative to entry of the current visit EMR data, at least the particular health care data and stored other EMR data to determine the specified analytic results data, wherein the stored other EMR data comprises historical and chronologically tracked demographic and EMR data relating to information of a plurality of past patients relevant to the particular analytical use case, including frequency of health care provider visits relevant to the particular analytical use case, and the particular health care data comprises the specified EMR data obtained during the current medical visit.

2. The system of claim 1, wherein the database system comprises one or more relational databases.

3. The system of claim 1, wherein the stored other EMR data includes stored EMR data that has never been received or parsed by the parser engine.

4. The system of claim 1, wherein the analytics and presentation engine is further configured to display at least a portion of the analytic results data.

5. The system of claim 1, wherein the health care data messages received by the parser engine comprises Health Level 7 (HL7) messages.

6. The system of claim 1, wherein the specified health care data is contained in particular segments and particular fields within the Health Level 7 (HL7) messages.

7. The system of claim 1, wherein the parser logic comprises:
    logic to identify particular subfields within the particular fields.

8. The system of claim 1, wherein the parser engine is a Python Flash API parser engine.

9. The system of claim 1, further comprising a Health Level 7 (HL7) messaging engine configured to:
    receive, in real time or near real time, current visit EMR data for one or more patients entered into at least one EMR system by a medical professional, staff member or system.

10. The system of claim 9, wherein the HL7 messaging engine comprises a Mirth Connect or Nextgen Connect interface engine.

11. The system of claim 1, wherein the health care data messages received by the parser engine originate from multiple EMR systems.

12. The system of claim 1, wherein the database system comprises:
    a relational database management system (RDBMS), utilizing Structured Query Language (SQL) and a temporal table structure for storage of both chronologically tracked historical EMR data and current EMR data.

13. The system of claim 1, wherein the analysis comprises utilizing one or more machine learning models.

14. The system of claim 1, wherein the database system comprises:
    a relational database management system (RDBMS), utilizing Structured Query Language (SQL), configured to manage the database system;
    wherein the RDBMS utilizes a set of tables that are designed to optimize or speed determination of analytic results data.

15. The system of claim 1, wherein the parser logic comprises:
    logic to identify particular medical site-specified z-segments within Health Level 7 (HL7) messages from the medical site.

16. The system of claim 1, wherein the parser logic comprises:
    logic to logically divide Health Level 7 (HL7) messages into segments.

17. The system of claim 1, wherein the parser logic comprises:
    logic to cause parsing of only Health Level 7 (HL7) messages that are determined to include one or more segments needed to determine specific analytic results data.

18. The system of claim 1, wherein the parser logic comprises:
    logic to determine efficient or optimal storage of extracted EMR data across one or more tables of the database system.

19. The system of claim 1, wherein the parser logic comprises:
    logic to, for efficiency, avoid extraction of EMR data already extracted from a previous health care data message.

20. The system of claim 1, wherein the analytics and presentation engine is configured to cause displaying, in real time or near real time relative to entry of the current visit EMR data, the analytic results data for use by a medical facility or a medical professional, comprising providing one or more user interface-based dashboards to display the analytic results data at the medical facility or to the medical professional.

21. A computer-implemented method for use with Electronic Medical Records (EMRs), the method comprising:
    receiving, in real time or near real time relative to entry of current visit EMR data into at least one EMR system by at least one user during a current medical visit, health care data messages including the current visit EMR data;
    using parsing logic, parsing, in real time or near real time relative to entry of the current visit EMR data, the health care data messages to identify and extract specified EMR data therefrom, wherein the specified EMR data comprises patient clinical data obtained during the current medical visit wherein the parsing logic comprises logic to identify particular segments within the health care data messages corresponding to the specified EMR data, and particular fields within the particular segments;
    in real time or near real time relative to entry of the current visit EMR data, receiving and storing the extracted specified EMR data in one or more relational databases comprising structuring elements comprising views and tables configured to enable determination of specified analytic results data including a risk assessment of an Emergency Department (ED) visit by the one or more patients occurring within a specified time period, based on a particular analytical use case related to the current visit;
    obtaining, from the one or more relational databases, in real time or near real time relative to entry of the current visit EMR data, particular health care data required to determine the specified analytic results data, wherein the particular health care data has passed through the parsing logic and comprises particular fields and segments corresponding to at least some of the specified EMR data; and
    analyzing, in real time or near real time relative to entry of the current visit EMR data, at least the particular health care data and stored other EMR data to determine the specified analytic results data, wherein the stored other EMR data comprises historical and chronologically tracked demographic and EMR data relating to information of a plurality of past patients relevant to the particular analytical use case related to the current visit, including frequency of health care provider visits relevant to the particular analytical use case, and the particular health care data comprises the specified EMR data obtained during the current medical visit.

22. A non-transitory computer readable medium or media containing one or more computer readable instructions for executing a method for use with Electronic Medical Records (EMRs), wherein the instructions, when executed by one or more processors, perform:
    receiving, in real time or near real time relative to entry of current visit EMR data into at least one EMR system by at least one user during a current medical visit, health care data messages including the current visit EMR data;
    using parsing logic, parsing, in real time or near real time relative to entry of the current visit EMR data, the health care data messages to identify and extract specified EMR data therefrom, wherein the specified EMR data comprises patient clinical data obtained during the current medical visit wherein the parsing logic comprises logic to identify particular segments within the health care data messages corresponding to the specified EMR data, and particular fields within the particular segments;
    in real time or near real time relative to entry of the current visit EMR data, receiving and storing the extracted specified EMR data in one or more relational databases comprising structural elements including views and tables configured to enable determination of specified analytic results data including a risk assessment of an Emergency Department (ED) visit by the one or more patients occurring within a specified time period, based on a particular analytical use case related to the current visit; and
    obtaining, from the one or more relational databases, in real time or near real time relative to entry of the current visit EMR data, particular health care data required to determine the specified analytic results data, wherein the particular health care data has passed through the parsing logic and comprises particular fields and segments corresponding to at least some of the specified EMR data; and
    analyzing, in real time or near real time relative to entry of the current visit EMR data, at least the particular health care data and stored other EMR data to determine the specified analytic results data, wherein the stored other EMR data comprises historical and chronologically tracked demographic and EMR data relating to information of a plurality of patients relevant to the particular analytical use case related to the current visit, including frequency of health care provider visits relevant to the particular analytical use case, and the particular health care data comprises the specified EMR data obtained during the current medical visit.

* * * * *